(12) United States Patent
Faries, Jr. et al.

(10) Patent No.: US 6,255,627 B1
(45) Date of Patent: Jul. 3, 2001

(54) THERMAL TREATMENT SYSTEM AND METHOD FOR MAINTAINING INTEGRITY AND ENSURING STERILITY OF SURGICAL DRAPES USED WITH SURGICAL EQUIPMENT

(75) Inventors: Durward I. Faries, Jr., McLean; Bruce R. Heymann, Vienna; Calvin Blankenship, Centerville, all of VA (US)

(73) Assignee: O.R. Solutions, INc., Chantilly, VA (US)

( * ) Notice: Subject to any disclaimer, the term of this patent is extended or adjusted under 35 U.S.C. 154(b) by 0 days.

(21) Appl. No.: 09/604,221

(22) Filed: Jun. 27, 2000

Related U.S. Application Data

(63) Continuation of application No. 09/046,090, filed on Mar. 23, 1998, now Pat. No. 6,901,058, which is a continuation-in-part of application No. 08/905,345, filed on Aug. 4, 1997, now Pat. No. 5,897,621, which is a continuation-in-part of application No. 08/427,938, filed on Apr. 26, 1995, now Pat. No. 5,653,938.

(51) Int. Cl.$^7$ .................................................. A61F 7/00
(52) U.S. Cl. .................. 219/430; 219/438; 219/433; 604/114; 604/291; 4/655
(58) Field of Search ................................ 219/430, 433, 219/438, 435, 452, 502, 506, 540, 552, 553; 128/898; 604/114, 291; 4/655

(56) References Cited

U.S. PATENT DOCUMENTS

| | | |
|---|---|---|
| 3,869,596 | 3/1975 | Howie . |
| 3,902,484 | 9/1975 | Wintes . |
| 4,270,067 | 5/1981 | Thomas et al. . |
| 4,284,880 | 8/1981 | Keiser . |
| 4,393,659 | 7/1983 | Keyes et al. . |
| 4,458,139 | 7/1984 | McClean . |
| 4,474,016 | 10/1984 | Winchell . |
| 4,522,041 | 6/1985 | Menzel . |
| 4,625,098 | 11/1986 | Joe . |
| 4,782,835 | 11/1988 | Bernardini . |
| 4,869,271 | 9/1989 | Idris . |
| 4,903,710 | 2/1990 | Jessamine et al. . |
| 4,934,152 | 6/1990 | Templeton . |
| 4,967,061 | 10/1990 | Weber, Jr. et al. . |
| 5,040,699 | 8/1991 | Gangemi . |

(List continued on next page.)

Primary Examiner—Teresa Walberg
Assistant Examiner—Shawntina Fuqua

(57) ABSTRACT

A thermal treatment system warming basin for warming a sterile liquid or medium includes a heating pad disposed on the exterior surface of the basin floor in various configurations (e.g., spiral, 'I', 'X' or serpentine configurations, multiple heating pad segments disposed about the basin floor, etc.) to prevent damage to a sterile surgical drape placed over the system when objects are placed within the basin. The configurations cover a portion of the basin floor to permit the basin to absorb thermal energy that may otherwise be absorbed by and cause damage to the drape. In addition, a thermal treatment system and corresponding sterile surgical drape may include a variety of mechanisms to ensure sterility of a sterile liquid within a basin. In particular, the drape may include a reflective material segment to reflect infrared light emitted from an infrared light source toward a detector to indicate the proper positioning and/or presence of the drape on the thermal treatment system. The infrared light source and corresponding detector may be disposed within the thermal treatment system below the basin or within the system top surface. Alternatively, magnetic media may be attached to the drape, while a magnetic detector is disposed within the thermal treatment system on the exterior surface of the basin floor or within the system top surface. The magnetic detector senses the drape magnetic media to detect the proper positioning and/or presence of the drape on the thermal treatment system.

20 Claims, 12 Drawing Sheets

U.S. PATENT DOCUMENTS

| | | |
|---|---|---|
| 5,042,455 | 8/1991 | Yue et al. . |
| 5,129,033 | 7/1992 | Ferrara et al. . |
| 5,163,299 | 11/1992 | Faries, Jr. et al. . |
| 5,174,306 | 12/1992 | Marshall . |
| 5,310,524 | 5/1994 | Campbell et al. . |
| 5,331,820 | 7/1994 | Faries, Jr. et al. . |
| 5,333,326 | 8/1994 | Faries, Jr. et al. . |
| 5,345,063 | 9/1994 | Reusche et al. . |
| 5,363,746 | 11/1994 | Gordon . |
| 5,374,813 | 12/1994 | Shipp . |
| 5,383,476 | 1/1995 | Peimer et al. . |
| 5,386,835 | 2/1995 | Elphick et al. . |
| 5,400,267 | 3/1995 | Denen et al. . |
| 5,400,616 | 3/1995 | Faries, Jr. et al. . |
| 5,402,644 | 4/1995 | Faries, Jr. et al. . |
| 5,429,801 | 7/1995 | Faries, Jr. et al. . |
| 5,435,322 | 7/1995 | Marshall . |
| 5,443,082 | 8/1995 | Mewburn . |
| 5,449,892 | 9/1995 | Yamada . |
| 5,457,962 | 10/1995 | Faries, Jr. et al. . |
| 5,463,213 | 10/1995 | Honda . |
| 5,502,980 | 4/1996 | Faries, Jr. et al. . |
| 5,522,095 | 6/1996 | Faries, Jr. et al. . |
| 5,524,478 | 6/1996 | Joy et al. . |
| 5,524,643 | 6/1996 | Faries, Jr. et al. . |
| 5,531,697 | 7/1996 | Olsen . |
| 5,539,185 | 7/1996 | Polster . |
| 5,551,240 | 9/1996 | Faries, Jr. et al. . |
| 5,615,423 | 4/1997 | Faries, Jr. et al. . |
| 5,653,938 | 8/1997 | Faries, Jr. et al. . |
| 5,658,478 | 8/1997 | Roeschel et al. . |
| 5,664,582 | 9/1997 | Szymaitiz . |
| 5,717,188 | 2/1998 | Vaillancourt . |
| 5,800,352 | 9/1998 | Ferre et al. . |
| 5,809,788 | 9/1998 | Faries, Jr. et al. . |
| 5,816,252 | 10/1998 | Faries, Jr. et al. . |
| 5,857,467 | 1/1999 | Faries, Jr. et al. . |
| 5,862,672 | 1/1999 | Faries, Jr. et al. . |
| 5,879,621 | 3/1999 | Faries, Jr. et al. . |
| 5,950,438 | 9/1999 | Faries, Jr. et al. . |
| 6,003,328 | 12/1999 | Faries, Jr. et al. . |
| 6,035,855 | 3/2000 | Faries, Jr. et al. . |
| 6,087,636 | 7/2000 | Faries, Jr. et al. . |
| 6,091,058 | 7/2000 | Faries, Jr. et al. . |

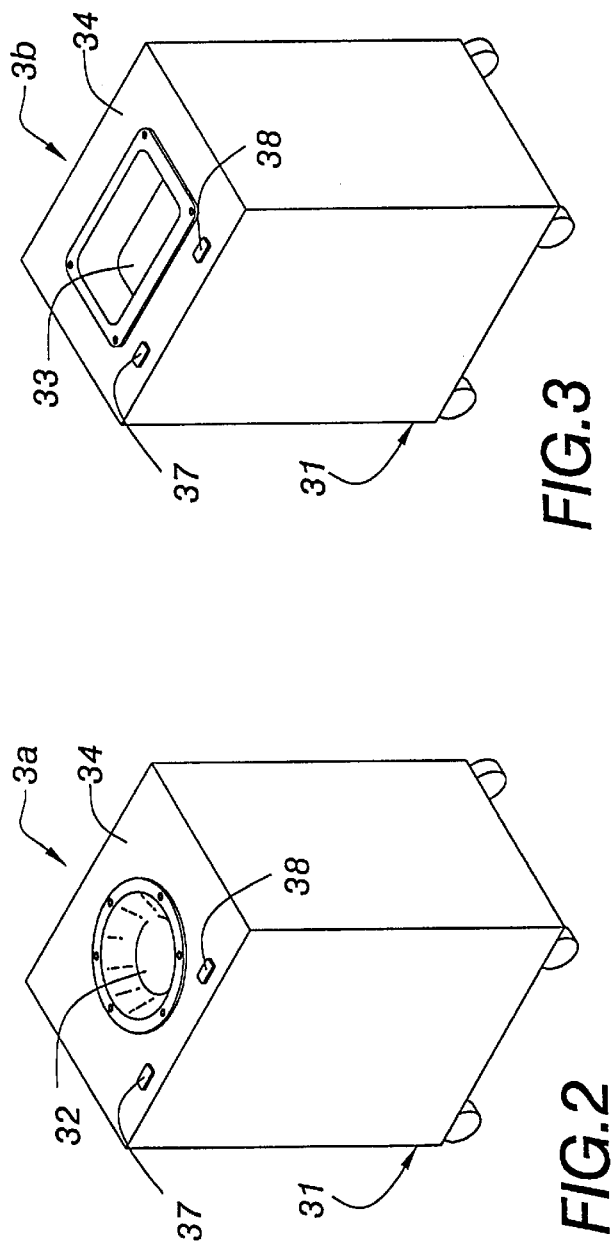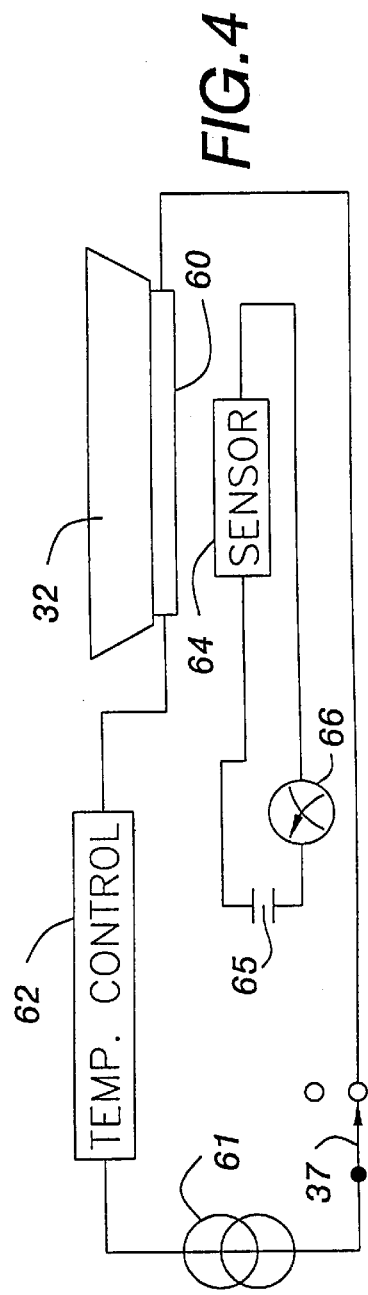

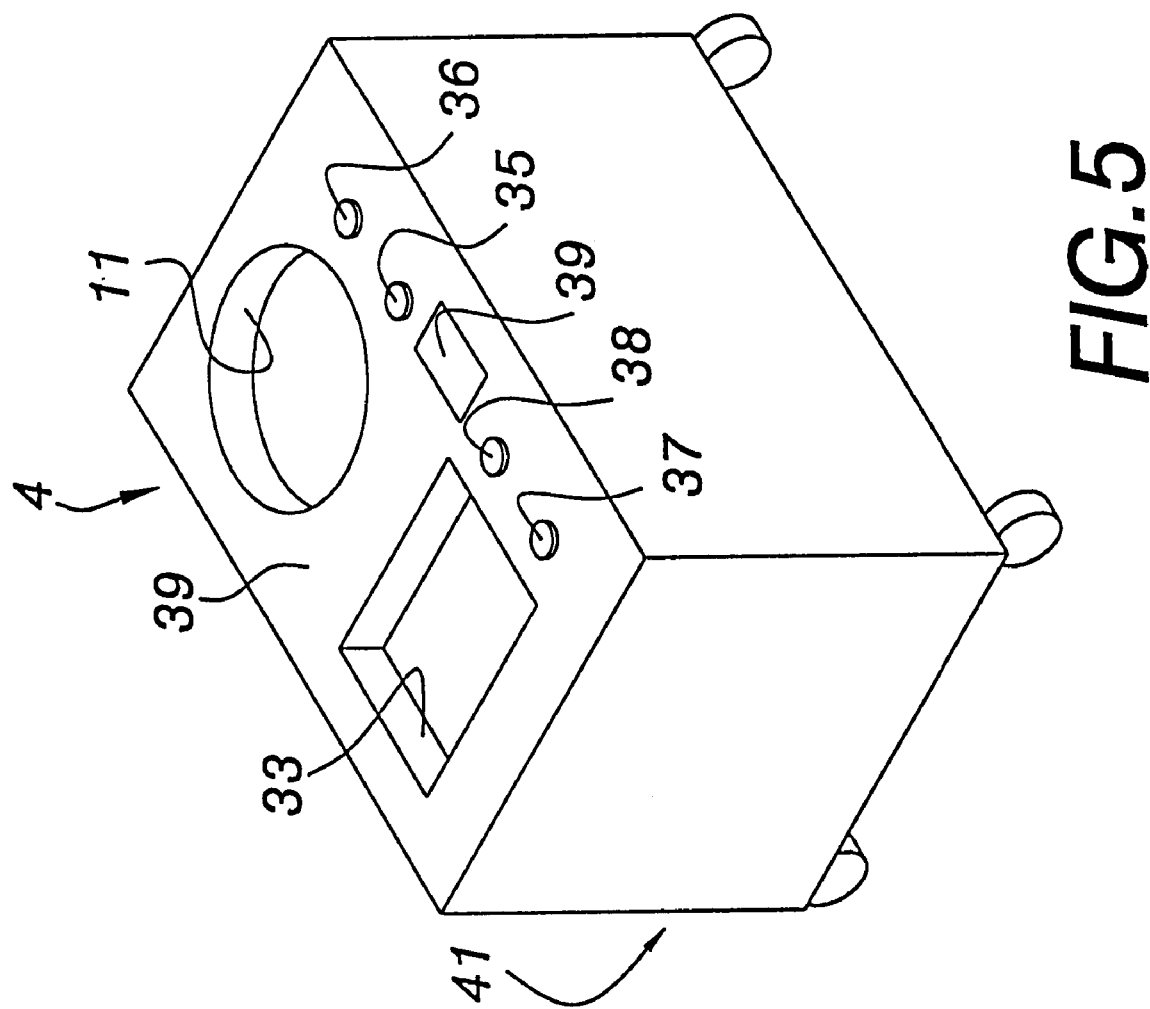

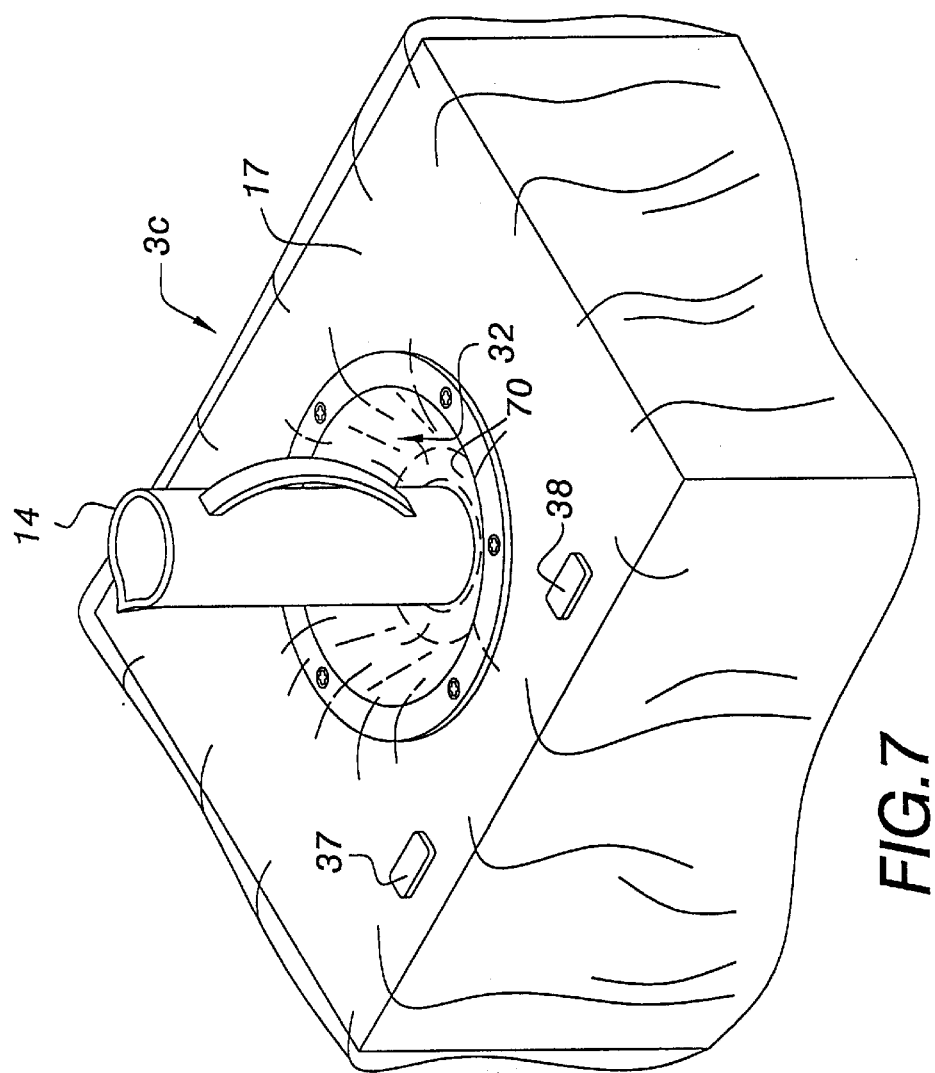
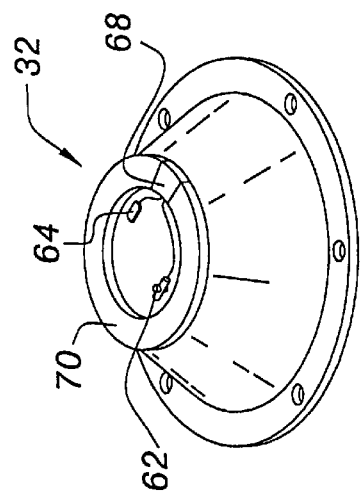
FIG. 7
FIG. 6

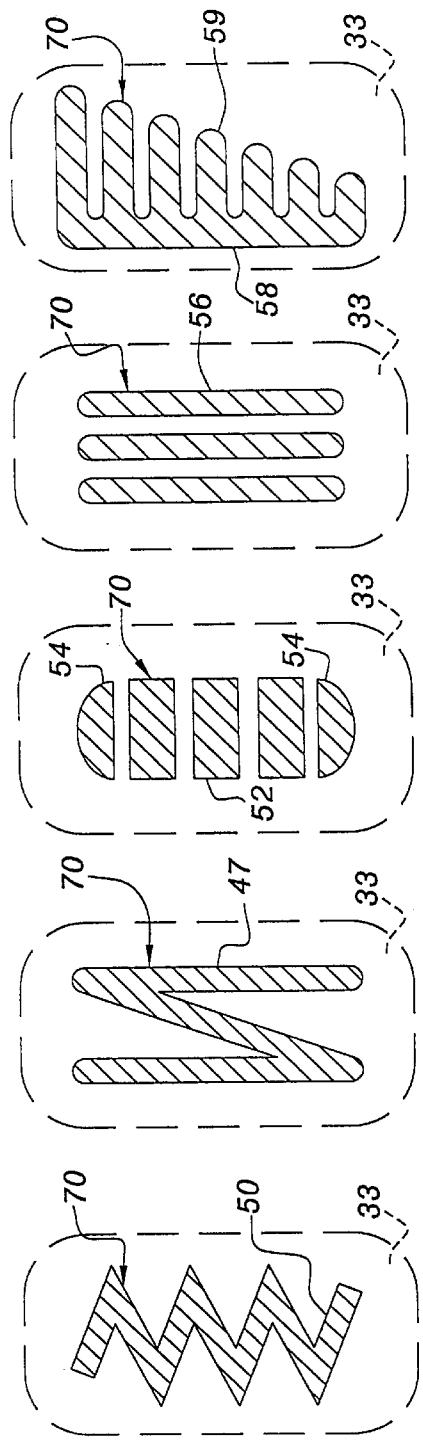

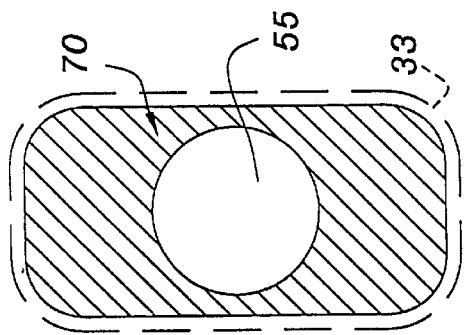
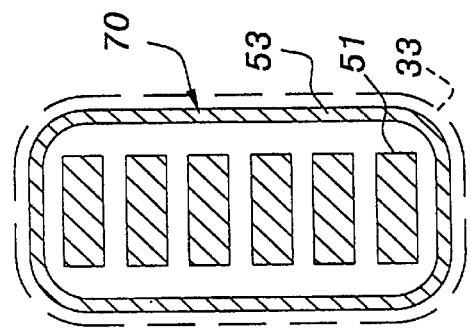
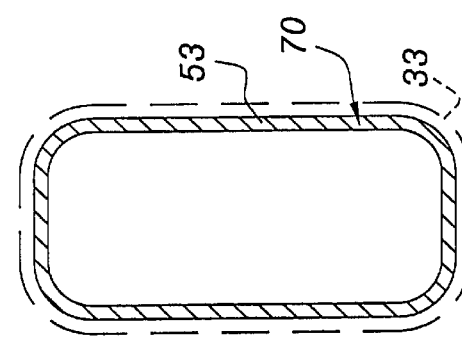
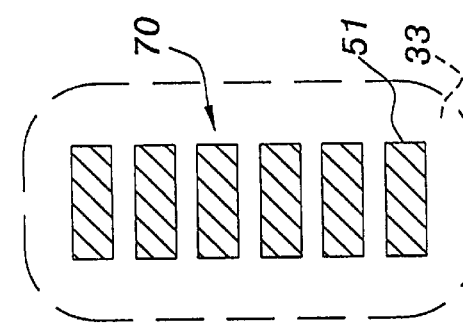
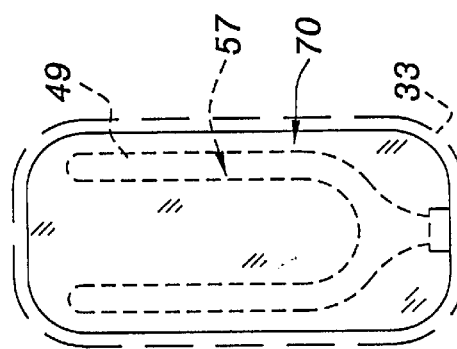

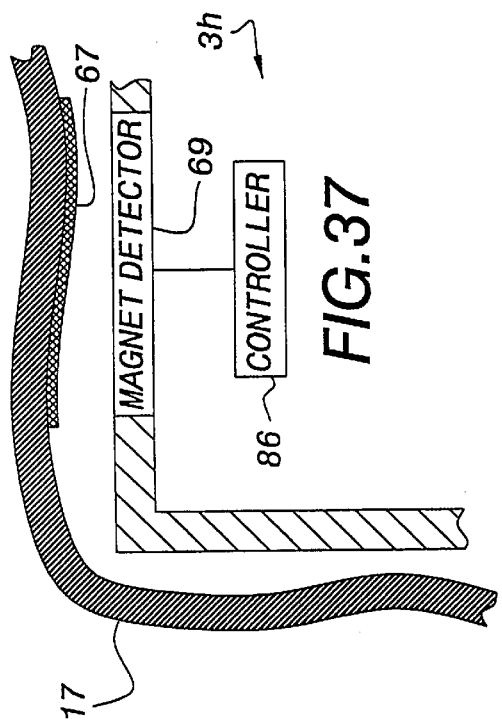
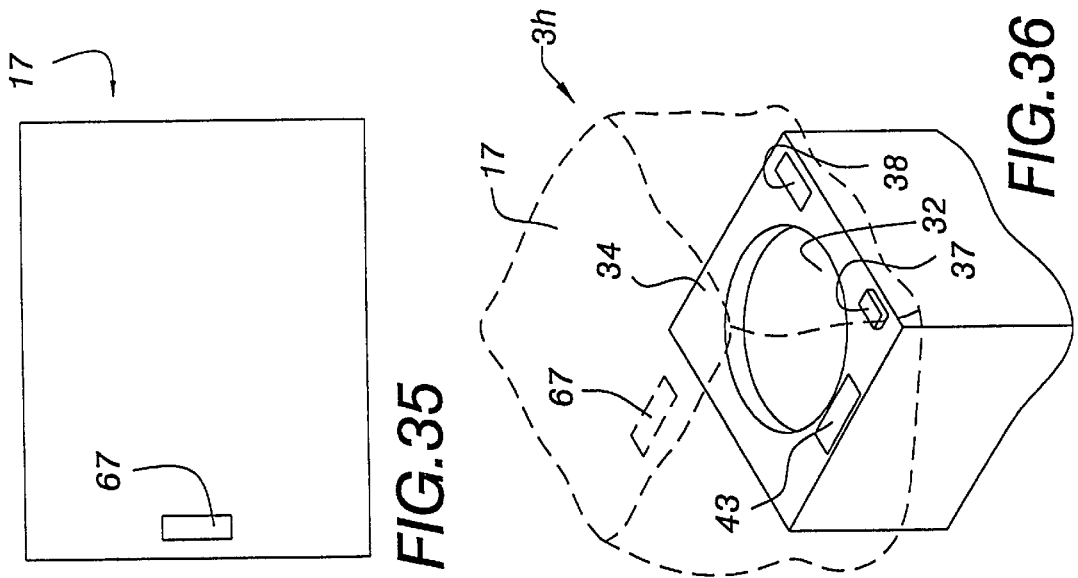

THERMAL TREATMENT SYSTEM AND METHOD FOR MAINTAINING INTEGRITY AND ENSURING STERILITY OF SURGICAL DRAPES USED WITH SURGICAL EQUIPMENT

CROSS-REFERENCE TO RELATED APPLICATIONS

This application is a continuation of U.S. patent application Ser. No. 09/046,090, entitled "Thermal Treatment System and Method for Maintaining Integrity and Ensuring Sterility of Surgical Drapes Used With Surgical Equipment", filed Mar. 23, 1998 now U.S. Pat. No. 6,091,058, which is a continuation-in-part of U.S. patent application Ser. No. 08/905,345, entitled "Method and Apparatus for Ensuring Sterility of Surgical Drapes Used with Surgical Equipment", filed Aug. 4, 1997 now U.S. Pat. No. 5,879,621, which is a continuation-in-part of U.S. patent application Ser. No. 08/427,938, entitled "Method and Apparatus for Ensuring Sterility of Surgical Drapes Used with Surgical Equipment", filed Apr. 26, 1995, now U.S. Pat. No. 5,653,938. The disclosures of the above-mentioned patent application and patents are incorporated herein by reference in their entireties.

BACKGROUND OF THE INVENTION

1. Technical Field

The present invention pertains to improvements in methods and apparatus for heating or cooling sterile surgical liquids and collecting surgical sterile slush. In particular, the present invention is an improvement of the methods and apparatus disclosed in U.S. Pat. No. 4,393,659 (Keyes et al), U.S. Pat. No. 4,934,152 (Templeton), U.S. Pat. No. 5,163,299 (Faries, Jr. et al), U.S. Pat. No. 5,331,820 (Faries, Jr. et al), U.S. Pat. No. 5,333,326 (Faries, Jr. et al), U.S. Pat. No. 5,457,962 (Faries, Jr. et al), U.S. Pat. No. 5,522,095 (Faries, Jr. et al), U.S. Pat. No. 5,524,643 (Faries, Jr. et al) and U.S. Pat. No. 5,615,423 (Faries, Jr. et al), and copending U.S. patent application Ser. No. 08/807,095, entitled "Surgical Drape and Stand for Use in Thermal Treatment Basins", filed Feb. 27, 1997. The disclosures of the aforementioned patents and copending patent application (i.e., U.S. patent application Ser. No. 08/807,095) are incorporated herein by reference in their entireties.

2. Discussion of Related Art

The above-referenced Keyes et al U.S. Pat. No. (4,393,659) discloses a surgical slush producing system having a cabinet with a heat transfer basin located at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton U.S. Pat. No. (4,934,152), the Keyes et al system has a number of disadvantages. In particular, the separate product basin must be removed and re-sterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. (5,163,299) notes that scraping congealed liquid from the drape is undesirable in view of the potential for damage to the drape, resulting in a compromise of sterile conditions. As a solution to the problem, the Faries, Jr. et al U.S. Pat. No. (5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The Faries, Jr. et al U.S. Pat. No. (5,331,820) resolves the problem of manual manipulation of the drape by providing a method and apparatus to automatically remove congealed liquid adhering to the drape without endangering the integrity of the drape. A flat disk or plate is typically provided at the bottom of the basin under the drape. The plate is moved in an up and down manner to manipulate the drape and disengage the congealed liquid adhering to the drape. The plate may be attached to a mechanism below the basin, or to the drape itself as disclosed in the Faries, Jr. et al U.S. Pat. No. (5,457,962).

In addition to accommodating surgical slush, the Templeton patent provides an electrical heater disposed at the bottom of the basin to convert sterile surgical slush to warmed sterile liquid, or to heat additional sterile liquid added to the basin. The electrical heater typically includes a heating element in the form of a thin wafer having a circular opening defined at the center of the heating element. A threaded stud projects through the opening to engage a heating plate via a nut and lock washer. The heating plate serves to dissipate excess heat from the heating element within a system cabinet and to aid in securing the heating element against the basin. The lock washer is typically constructed of an insulating material to minimize heat transfer between the heating element and stud, thereby preventing formation of a hot spot at the center of the basin floor that may melt the drape during system operation. The Templeton patent describes the need for warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. For example, if the surgical slush is not of a desired consistency (e.g., too thick), the availability of warm sterile liquid to be added to the slush permits rapid adjustability of slush consistency. Likewise, maintaining instruments at or near body temperature during surgery is a desirable feature permitted by warm sterile liquid. Generally, if warm sterile liquid is simultaneously available with surgical slush, there is no need to wait for the slush to melt at the end of the surgical procedure. Moreover, the simultaneous provision of sterile surgical slush and warm sterile liquid permits the two to be comprised of different compounds as is sometimes necessary for various surgical procedures.

In response to the foregoing need for simultaneous availability of warmed sterile liquid and sterile surgical slush, the Faries, Jr. et al U.S. Pat. Nos. (5,333,326, 5,522,095 and 5,524,643) disclose a thermal treatment system of the type having at least a warming basin for containing warm surgical liquid and a surgical slush or cooling basin of the type disclosed in the Templeton patent. The warming basin may be implemented as a separate unit and secured to a preexisting surgical slush system (e.g., a thermal treatment system having a cooling basin to produce surgical slush), may be constructed as part of an integral cabinet that houses warming and cooling basins, or may be implemented as a separate unit and attached to an individual surgical slush unit a (e.g., a cooling basin producing surgical slush that is implemented as an individual unit) with the warming and surgical slush units supported by a common base. A large surgical drape covers both the warming and cooling basins and contains the warm surgical liquid and surgical slush in a sterile manner. In addition, the drape may include centering indicia to direct placement of the drape over the thermal treatment system and within each basin.

Typically, a sterile surgical drape is placed over a single or multiple basin thermal treatment system with a portion of the drape disposed within each thermal treatment system basin to form a drape receptacle within each basin for containing a sterile liquid or medium. The sterile liquid contained and warmed within a thermal treatment system warming basin may be utilized to heat objects (e.g., medical instruments, containers, pitchers, etc.) placed within that basin. However, placement of objects within the warming basin may puncture the drape in several different ways, thereby compromising sterility of the warm sterile liquid and possibly an entire surgical procedure. For example, objects placed within the warming basin may trap air between the object base and drape material. The trapped air typically expands beneath the object when heated and expels sterile liquid from beneath the object, thereby permitting the drape to absorb additional thermal energy from the warming basin at locations where liquid has been expelled. The additional thermal energy causes the drape to overheat, melt and stick to the warming basin, thereby forming holes. Further, the drape material may soften significantly when exposed to the heated basin floor, thereby allowing normally safe (e.g., dull or blunt) objects to puncture the material (e.g., blunt plastic syringe tips and blunt tipped hemostats). Moreover, lack of sufficient liquid in the warming basin due to user error or evaporation tends to increase the amount of thermal energy absorbed by the drape, thereby causing portions of the drape to overheat forming hot spots and pinholes. Since a warming basin heater covers substantially the entire basin floor, the basin is continuously supplied or saturated with thermal energy from that heater and cannot further conduct thermal energy to reduce the amount of thermal energy absorbed by the drape, thereby enabling drape damage as described above.

Heating stainless steel objects within the warming basin, such as pitchers or graduates, tends to reduce drape damage since the stainless steel objects conduct heat from the contact site (e.g., contact site between the object and drape or basin), thereby reducing the amount of thermal energy absorbed by the drape. However, stainless steel objects tend to be expensive, while a substantial amount of medical objects are constructed of plastic. The plastic objects absorb a minimal amount of thermal energy, thereby enabling the drape to absorb thermal energy from the warming basin in amounts sufficient to cause damage to the drape as described above. The Templeton patent attempts to overcome the problem of drape melting within a warming basin during system operation by preventing formation of a hot spot at the center of the basin floor. This is accomplished by minimizing heat transfer between a heating element located at the bottom of the basin and a stud, disposed adjacent the basin bottom, that extends through a heating element central opening as described above. However, the stud and/or heating element central opening each are of a relatively small size in comparison with the basin floor and cannot conduct sufficient amounts of thermal energy to substantially reduce the amount of thermal energy absorbed by the drape when objects are placed in the basin. Thus, the drape is permitted to absorb excess thermal energy from the warming basin that may damage the drape in substantially the same manner described above when objects are placed in the basin.

Copending U.S. patent application Ser. No. 08/807,095, discloses a system to overcome the aforementioned problems of heating objects within warming basins by including a stand to elevate the objects above the heated basin floor and prevent damage to a drape. The stand may be implemented as a separate unit for placement within a warming basin or be disposed on and integral with the drape. However, the technique disclosed in the copending application may stand some improvement. In particular, it is desirable to prevent damage to the drape when heating objects within the warming basin without introducing additional components into the system that may require sterilization or replacement prior to each use, thereby creating additional chores for operating room personnel. For example, operating room personnel may be required to sterilize the stand and/or verify the presence of the stand within the warming basin prior to heating objects within that basin to ensure sterile conditions. Further, additional system components tend to increase system complexity and cost, while providing another manner in which the sterile liquid or medium contained within the warming basin may become contaminated during a surgical procedure.

Generally, a sterile surgical drape is disposed over a thermal treatment system as described above to essentially form a sterile field above each basin to maintain sterility of a sterile liquid or medium. Since the sterile surgical drape provides a sterile field above each basin for the sterile liquid, it is important that the drape be properly positioned on the thermal treatment system to prevent contamination of the sterile liquid and a surgical procedure. Accordingly, the Faries, Jr. et al U.S. Pat. No. (5,615,423) discloses a surgical drape having various indicia to assist an operator in properly placing the surgical drape over the thermal treatment system and within warming and/or cooling basins to ensure sterility of the sterile liquid. The indicia may be disposed on drapes for use with single or multiple basin thermal treatment systems. In addition, the aforementioned Faries, Jr. et al U.S. Pat. Nos. (5,333,326, 5,522,095 and 5,524,643) disclose a surgical drape for a multiple basin thermal treatment system having centering indicia to direct placement of the drape on the thermal treatment system and within each thermal treatment basin as described above.

The apparatus and/or drapes disclosed in the above-mentioned patents may stand some improvements to ensure sterile conditions. In particular, the Faries, Jr. et al U.S. Pat. Nos. (5,333,326, 5,522,095, 5,524,643 and 5,615,423) disclose drapes having indicia to facilitate proper deployment of the drapes on a thermal treatment system as described above, however, operating room personnel or other users determine whether or not a drape is properly positioned on the thermal treatment system, thereby providing a margin for human error that may produce non-sterile conditions from an improperly positioned drape. Further, the drape generally requires continuous monitoring during system operation to ensure that the drape maintains its position on the thermal treatment system to provide the sterile field. If the drape is improperly positioned or shifts during system operation, the sterile field may become contaminated, thereby compromising the sterility of the entire surgical procedure. Although operating room personnel can be advised and cautioned about the importance of properly placing a drape over a thermal treatment system prior to the performance of a surgical procedure, there is no assurance that carelessness will not result in operation of a thermal treatment system without the proper placement and/or use of the drape on the system. Thus, it is desirable to automatically detect the proper positioning and/or presence of a drape on a thermal treatment system to ensure the drape provides a sterile field and maintains sterility of sterile liquid during a surgical procedure.

OBJECTS AND SUMMARY OF THE INVENTION

Accordingly, it is an object of the present invention to prevent puncturing of a surgical drape disposed over a thermal treatment system and within a thermal treatment system warming basin when objects (e.g., medical instruments, containers, pitchers, etc.) are placed in that basin.

It is another object of the present invention to prevent puncturing of a surgical drape disposed over a thermal treatment system and within a thermal treatment system warming basin by utilizing a heating pad arranged in various configurations to cover a portion of the warming basin floor and enable the basin to absorb thermal energy that may otherwise be absorbed by and cause damage to the drape.

Yet another object of the present invention is to automatically ensure the sterility of a sterile medium contained within a thermal treatment system basin by enabling operation of the thermal treatment system upon detecting the proper positioning and/or presence of a sterile surgical drape placed over the thermal treatment system, the drape providing a sterile field above the basin to maintain sterility of the sterile medium.

Still another object of the present invention is to ensure sterility of a sterile medium contained within a thermal treatment system basin by detecting the proper positioning and/or presence of a sterile surgical drape placed over a thermal treatment system via an infrared light source and detector disposed below the basin, whereby detection by the detector of infrared light emitted from the infrared light source and reflected by the drape indicates the proper positioning and/or presence of the drape on the thermal treatment system.

A further object of the present invention is to ensure sterility of a sterile medium contained within a thermal treatment system basin by detecting the proper positioning and/or presence of a sterile surgical drape placed over a thermal treatment system via an infrared light source and detector disposed within a thermal treatment system top surface whereby detection by the detector of infrared light emitted from the infrared light source and reflected by the drape indicates the proper positioning and/or presence of the drape on the thermal treatment system.

Yet another object of the present invention is to ensure sterility of a sterile medium contained within a thermal treatment system basin by detecting the proper positioning and/or presence of a sterile surgical drape placed over a thermal treatment system via magnetic media attached to the drape and a magnetic detector disposed below the basin, whereby detection of the drape magnetic media by the magnetic detector indicates the proper positioning and/or presence of the drape on the thermal treatment system.

Still another object of the present invention is to ensure sterility of a sterile medium contained within a thermal treatment system basin by detecting the proper positioning and/or presence of a surgical drape placed over thermal treatment system via magnetic media attached to the drape and a magnetic detector disposed within a thermal treatment system top surface, whereby detection of the drape magnetic media by the magnetic detector indicates the proper positioning and/or presence of the drape on the thermal treatment system.

The aforesaid objects are achieved individually and in combination, and it is not intended that the present invention be construed as requiring two or more of the objects to be combined unless expressly required by the claims attached hereto.

According to the present invention, a thermal treatment system warming basin for warming a sterile liquid or medium includes a heating pad disposed on the exterior surface of the basin floor in various configurations to prevent damage to a sterile surgical drape, placed over the thermal treatment system and within the warming basin, when objects are placed in the basin. The heating pad applies thermal energy to the warming basin to heat the sterile liquid and objects (e.g., medical instruments, containers, pitchers, etc.) placed within the basin. The heating pad may be disposed on the basin floor in various configurations (e.g., spiral, 'I', 'X' or serpentine configurations, multiple heating pad segments disposed about the basin floor, etc.) that cover a portion of the basin floor to permit the basin to absorb thermal energy that may otherwise be absorbed by and cause damage to the drape.

In addition, a thermal treatment system and corresponding sterile surgical drape may include a variety of mechanisms to ensure sterility of a sterile liquid or medium contained within a thermal treatment system basin. The mechanisms enable operation of the thermal treatment system upon detection of the proper positioning and/or presence of a surgical drape placed over the thermal treatment system, the drape providing a sterile field above the basin to maintain sterility of the sterile liquid. In particular, an infrared light source and corresponding detector may be disposed within the thermal treatment system below the basin to detect the proper positioning and/or presence of the drape on the thermal treatment system. The drape includes a reflective material segment and is placed over the thermal treatment system such that the reflective material segment is coincident the infrared light source and detector. The basin floor typically includes a window to permit emission and detection of infrared light, while the drape reflective material may serve as placement indicia to direct placement of the drape over the thermal treatment system and within the basin.

Infrared light emitted from the infrared light source and through the window is reflected by the drape reflective material segment back through the window toward the detector to indicate the proper positioning and/or presence of the drape on the thermal treatment system. Upon detecting the infrared light, the detector enables thermal treatment system operation.

Alternatively, the infrared light source and detector may be disposed within the thermal treatment system top surface with the reflective material segment disposed on the drape such that the reflective material segment is positioned proximate the infrared light source and detector when the drape is placed over the thermal treatment system. The reflective material segment may be disposed on the drape to serve as placement indicia for directing placement of the drape over the thermal treatment system and within the basin in a similar manner as described above. The infrared light source and detector sense the proper positioning and/or presence of the drape on the thermal treatment system in substantially the same manner described above.

The proper positioning and/or presence of a surgical drape placed on a thermal treatment system may also be detected via magnetic media. Specifically, magnetic media may be attached to the drape, while a magnetic detector is disposed within the thermal treatment system below the basin on the exterior surface of the basin floor. The magnetic media may be disposed on the drape to serve as placement indicia for directing placement of the drape over the thermal treatment system and within the basin. The drape is placed over the thermal treatment system with the drape magnetic media positioned proximate or in a location detectable by the magnetic detector. The magnetic detector senses the drape magnetic media to detect the proper positioning and/or presence of the drape on the thermal treatment system. Upon detecting the magnetic media, the magnetic detector enables thermal treatment system operation. Alternatively, the magnetic detector may be disposed within a thermal treatment system top surface with the magnetic media positioned proximate the magnetic detector when the drape is placed over the thermal treatment system. The magnetic media may be disposed on the drape to serve as placement indicia for directing placement of the drape over the thermal treatment system and within the basin in a similar manner as described above. The magnetic detector senses the proper positioning and/or presence of the drape on the thermal treatment system in substantially the same manner described above.

The infrared and magnetic drape detection techniques described above may be utilized for any warming or cooling basins of single or multiple basin thermal treatment systems. Similarly, the warming basin having various heating pad configurations described above may be implemented independently of or in combination with the infrared or magnetic drape detection techniques described above in single basin or multiple basin thermal treatment systems.

The above and still further objects, features and advantages of the present invention will become apparent upon consideration of the following detailed description of the specific embodiments thereof, particularly when taken in conjunction with the accompanying drawings wherein like reference numerals in the various figures are utilized to designate like components.

BRIEF DESCRIPTION OF THE DRAWINGS

FIG. 2 is a view in perspective of a thermal treatment system of the type employed by the present invention containing a substantially circular warming basin for warming a sterile liquid.

FIG. 3 is a view in perspective of a thermal treatment system of the type employed by the present invention containing a substantially rectangular warming basin for warming a sterile medium.

FIG. 4 is an electrical schematic diagram of an exemplary heating unit employed by the thermal treatment system of FIG. 2.

FIG. 5 is a view in perspective of a multiple basin thermal treatment system of the type employed by the present invention.

FIG. 6 is a view in perspective of a substantially circular thermal treatment system warming basin including a substantially annular heating pad extending about a basin floor exterior surface toward the basin floor periphery according to the present invention.

FIG. 7 is a view in perspective of an object placed on a surgical drape disposed over a thermal treatment system having the substantially circular warming basin of FIG. 6.

FIGS. 10–23 are top views in plan of substantially rectangular thermal treatment system warming basins including heating pads having various configurations to heat sterile liquid and objects contained within drape receptacles formed in the basins without damaging the drape according to the present invention.

FIG. 24 is a top view in plan of a substantially rectangular thermal treatment system warming basin including a heating pad having a heating element configured to cover a portion of the warming basin floor to heat sterile liquid and objects contained within a drape receptacle formed in the basin without damaging the drape according to the present invention.

FIG. 35 is a top view in plan of surgical drape having magnetic media disposed toward a drape edge for detection by a magnetic detector embedded within a thermal treatment system top surface to indicate the proper positioning and/or presence of the drape on a thermal treatment system according to the present invention.

FIG. 36 is an exploded view in perspective of the surgical drape of FIG. 35 placed over a thermal treatment system including a warming basin having a generally annular heating pad configuration, and a magnetic detector embedded within a thermal treatment system top surface for detecting the drape magnetic media to verify the proper positioning and/or presence of the drape on the thermal treatment system and to enable thermal treatment system operation.

FIG. 37 is a side view in elevation and partial section of the thermal treatment system of FIG. 36 schematically illustrating the magnetic detector disposed within a thermal treatment system top surface for detecting the proper positioning and/or presence of the drape on the thermal treatment system and enabling thermal treatment system operation.

DESCRIPTION OF THE PREFERRED EMBODIMENTS

Figure 1:
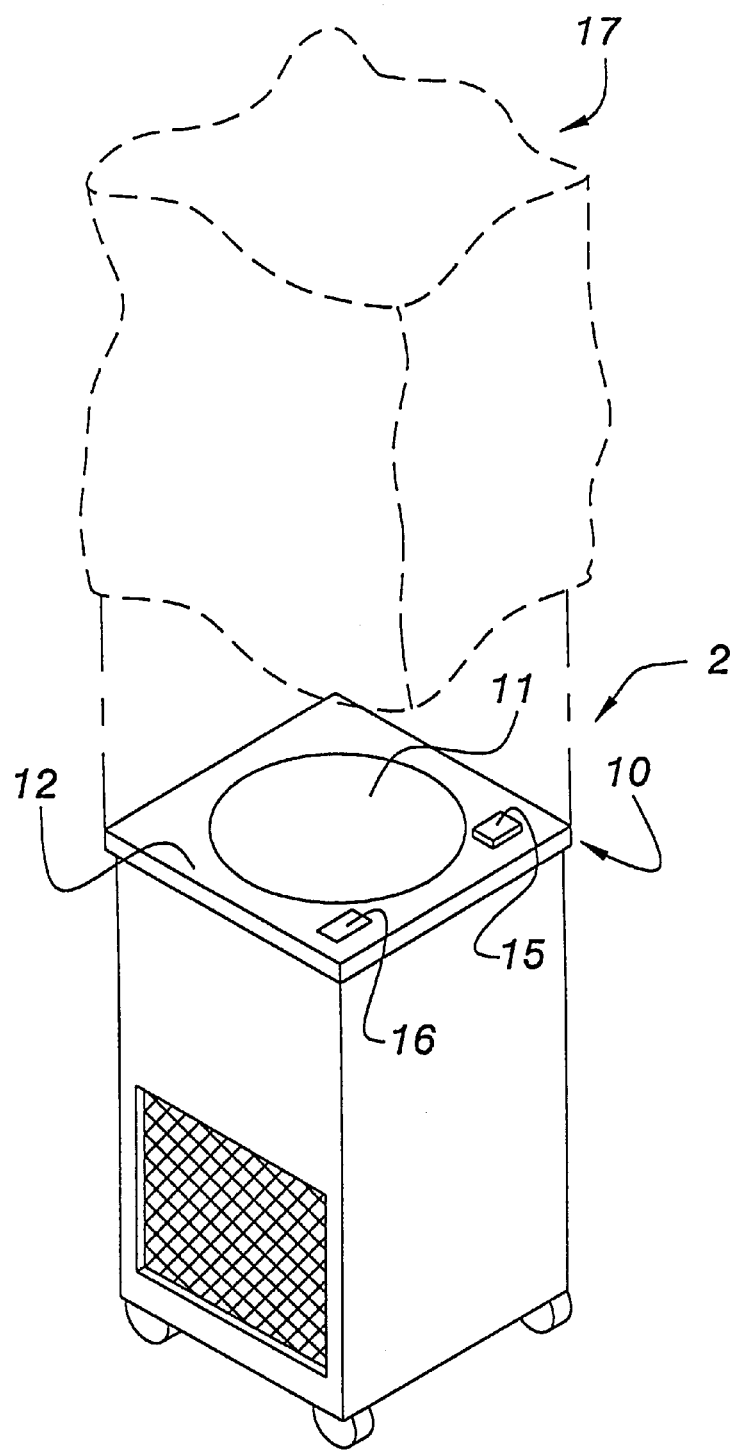
FIG. 1 is an exploded view in perspective of a surgical drape placed over a thermal treatment system of the type employed by the present invention for cooling or congealing a sterile liquid.

An exemplary thermal treatment system and surgical drape of the type employed by the present invention to cool or congeal a sterile liquid or medium is illustrated in FIG. 1. Specifically, a thermal treatment system 2 includes a cabinet 10 with a top surface 12 having a basin 11 mounted thereon in an appropriately sized recess. Basin 11 is made of thermally conductive material, typically stainless steel, and includes a generally flat bottom wall and frusto-conical side walls. It is to be understood that the terms "up", "down", "upper", "lower", "top", "bottom", "front", "rear", "back", "side", "left", "right", "length", "width" and "thickness" are utilized herein merely to described points of reference and do not limit the present invention to any specific orientation or configuration. A conventional refrigeration unit (not shown) is disposed within cabinet 10 and typically includes a compressor, a condenser and an expansion control unit connected by appropriate fluid conduits in a closed refrigeration loop with an evaporator (not shown). The evaporator is in the form of a coil wound about the exterior surface of basin 11 in thermal transfer relation therewith. When the refrigeration unit is activated via appropriate controls 15 and temperature control 16, the evaporator cools the sidewall of basin 11 to a temperature substantially below the freezing temperature of liquid used in forming sterile slush. This temperature is preferably on the order of −32° F. to 10° F. For an example of the structure and operation of a refrigeration unit, reference is made to the aforementioned Keyes et al and Templeton patents.

A sterile surgical drape 17, preferably transparent, is disposed over the top and sides of cabinet 10 and made to conform to the side walls and bottom of basin 11. The portion of surgical drape 17 disposed in the basin serves as a sterile receptacle for sterile liquid placed therein to be cooled to the desired sterile slush consistency. Typical sterile liquid used by thermal treatment systems (e.g., systems that warm, cool or congeal sterile liquid) is a 0.80% to 0.95% sodium chloride solution (e.g., saline). The drape illustrated in FIG. 1 is of the fitted type (i.e., contoured and seamed to fit to the cabinet), however, it is to be understood that the present invention equally applies to non-fitted drapes that simply hang loosely over the cabinet sides.

When the thermal treatment system is operating, the sterile liquid in the drape receptacle freezes in pieces on the surgical drape portions covering the side walls of the basin. The thermal treatment system may further include a dislodgement mechanism for automatically removing frozen pieces of the sterile liquid from the surgical drape portions covering the basin walls to form sterile slush. For example, the dislodgement mechanism may include a motor and a shaft that extends from the motor to a plate disposed at the bottom of the basin beneath the drape receptacle. The motor reciprocates the shaft up and down, while the shaft, in turn, moves the plate up and down to manipulate the bottom of the drape receptacle and loosen attached pieces of frozen sterile liquid (e.g., saline). For examples of the above-described and other types of dislodgement mechanisms, reference is made to the patents and copending applications mentioned above.

A typical thermal treatment system of the type employed by the present invention for heating a sterile liquid or medium is illustrated in FIG. 2. Specifically, a thermal treatment system 3a includes a cabinet or housing 31 and a warming basin 32 recessed into a top surface 34 of cabinet 31. Basin 32 is made of a thermally conductive material, typically stainless steel, and, by way of example only, is illustrated as being substantially circular with a generally flat bottom wall and frusto-conical side walls. The basin further includes an open top portion to receive the sterile liquid. A heater power switch 37 and a temperature controller/indicator 38 are provided on top surface 34 adjacent the warming basin.

Alternatively, the thermal treatment system may include a substantially rectangular basin as illustrated in FIG. 3. Specifically, thermal treatment system 3b is substantially similar to system 3a described above except that system 3b includes substantially rectangular basin 33. Basin 33 is made of a thermally conductive material, typically stainless steel, and includes bottom and side walls that collectively define a basin interior. The basin further includes an open top portion to receive the sterile liquid, while the bottom and side walls interface smoothly to provide the basin with rounded corners.

An exemplary manner of heating sterile liquid contained within a warming basin is illustrated schematically in FIG. 4. By way of example only, the manner of heating sterile liquid contained within a warming basin is described below with reference to substantially circular basin 32 (FIG. 2), however, this manner of heating sterile liquid may be applied to any shaped warming basin, such as substantially rectangular basin 33 (FIG. 3). Specifically, an electrical circuit includes a power source 61 connected in series with a temperature control unit or thermostat 62, a heating pad or heater 60, and power control switch 37. Thermostat 62 receives control signals from temperature controller/indicator 38 (FIG. 2) to control heating pad 60. Heating pad 60 is typically a thin wafer-like member disposed along and covering a substantial portion of the bottom exterior surface of warming basin 32, secured to the basin by a suitable pressure sensitive adhesive having efficient heat transfer characteristics. Heating pad 60, for example, may be of the type described in the aforementioned Templeton patent. Temperature control unit 62 includes a device for adjusting current passing through heating pad 60 so as to permit selective adjustment of heat applied to liquid contained within basin 32. Power switch 37 permits selective application and removal of current flow with respect to heating pad 60.

A temperature sensor 64 is disposed adjacent basin 32 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to temperature controller/indicator 38 described above. For an example of structures and operation of a heating unit, reference is made to the Faries, Jr. et al U.S. Pat. No. (5,333,326) and other above-mentioned patents and copending applications.

It is to be understood that the thermal treatment systems described above may have various configurations and include a plurality of basins warming and/or cooling a sterile liquid. An example of such a system containing both a slush generating unit and a sterile liquid warming unit is illustrated in FIG. 5. Specifically, system 4 includes an integral assembly 41 having a cooling basin 11 for producing surgical slush and a warming basin 33 for heating sterile liquid recessed into a top surface 39 of a common cabinet. The cooling and warming basins, by way of example only, are substantially similar to the cooling and warming basins described above for FIGS. 1 and 3, respectively. Also disposed on top surface 39 are cooling unit power switch 35, a cooling unit temperature controller/indicator 36, a heater power switch 37 and heater unit temperature controller/indicator 38. A sterile surgical drape (not shown) suitable for covering the entire top surface 39 is placed over the thermal treatment system and pushed down into basins 11, 33 to form drape receptacles within the basins to contain the sterile liquid as described above. For further examples of multiple basin thermal treatment systems, reference is made to the above-mentioned Faries, Jr. et al patents U.S. Pat. Nos. (5,333,326, 5,522,095 and 5,524,643).

A sterile surgical drape suitable for placement over a thermal treatment system is constructed of a material that is impervious to heated liquid and cooled slush, and is sufficiently soft and flexible to conform to basin walls and form a drape receptacle within a thermal treatment system basin. The thickness of the drape is preferably minimized to render thermal transfer therethrough most efficient, yet the thickness is sufficient to resist tearing and puncturing of the drape during normal use. Typically, a drape is made of materials commonly used in hospitals for surgical drapes and has a thickness, by way of example only, in the range of 4.5 to 6.0 mils. The drape may also be made of polyurethane film as disclosed for the drape in the aforementioned Templeton patent. The drape is designed to be disposable after a single use and is provided presterilized and prepackaged in a leak-proof plastic bag or other sealed container to preserve the sterile nature of the drape during storage.

A surgical drape is typically placed over a thermal treatment system and covers the top surface and hangs down the sides of the system cabinet, while a portion of the drape is pushed down into, and conforms to, each basin to form a drape receptacle within that basin for containing heated liquid or surgical slush. The drape may be non-fitted or flat (e.g., a plain or basic drape of sufficient length that is placed over the thermal treatment system) or may be constructed such that the drape is formed to the contour of the cabinet housing for a more precise fit (e.g., a fitted drape). Generally, objects (e.g., medical instruments, containers, pitchers, etc.) may be placed within the warming basin to be heated by warmed sterile liquid contained by the drape receptacle formed in that basin. However, placement of objects in the warming basin may trap air between the object base and the drape such that the trapped air expands when heated and expels liquid from the proximity of the drape. Consequently, the drape absorbs additional thermal energy from the basin coincident locations where the liquid has been expelled. The absorption of additional thermal energy may cause the drape to overheat, melt and stick to the basin, thereby forming holes. Further, the drape may soften when exposed to the heated area of the basin, thereby becoming susceptible to punctures from normally blunt, dull or "safe" objects (e.g., blunt plastic syringe tips and blunt tipped hemostats). Moreover, additional absorption of thermal energy by the drape, and hence puncturing, may occur due to lack of sufficient liquid in the basin via evaporation or user error. Since a warming basin heater covers substantially the entire basin floor, the warming basin is continuously supplied or saturated with thermal energy from that heater and cannot further conduct thermal energy in a manner to reduce the amount of thermal energy absorbed by the drape, thereby enabling damage to the drape as described above.

Medical objects constructed of stainless steel tend to reduce drape damage since these objects conduct heat from the site of contact (e.g., between the object and drape or basin) and prevent the drape from absorbing thermal energy sufficient to cause the drape to burn and/or melt. However, a substantial portion of medical objects are constructed of plastic and do not conduct heat from the contact site, thereby enabling the drape to absorb excess thermal energy.

A substantially circular warming basin having a heating pad disposed about the basin floor exterior surface toward the basin floor periphery to enable the basin to absorb thermal energy that may otherwise damage a surgical drape when objects are placed within that basin is illustrated in FIG. 6. Warming basin 32 is substantially similar to the substantially circular warming basin described above for FIG. 2, and is illustrated in FIG. 6 in an inverted position relative to use within a thermal treatment system for descriptive purposes. However, the basin is mounted within a thermal treatment system in substantially the same manner illustrated in FIG. 7. Specifically, basin 32 includes a heating pad 70, a thermostat 62 and a temperature sensor 64, each disposed on the basin floor exterior surface. Heating pad 70 is substantially annular and is preferably disposed about the basin floor exterior surface toward the basin floor periphery (e.g., toward the junction between the basin side and bottom walls). The heating pad is typically implemented by an etched foil silicone rubber heater (e.g., 120V, 250 watt heater) attached to the basin via pressure sensitive adhesives and includes an extra layer of silicone rubber on the adhesive side of the heating pad facing the basin floor exterior surface. By way of example only, heating pad 70 includes an inner diameter (i.e., diameter of a heating pad opening) of approximately seven inches, an outer diameter of approximately nine inches and a thickness extending between the inner and outer diameters of approximately two inches.

Thermostat 62 and temperature sensor 64 are substantially similar to the thermostat and temperature sensor described above, and function along with temperature controller/indicator 38 (FIG. 7) to control heating pad 70 to heat sterile liquid contained within basin 32 in substantially the same manner described above for FIG. 4. Thermostat 62 is typically implemented by a conventional thermostat and is disposed on the basin floor exterior surface within the confines of the heating pad to control the heating pad as described above. Temperature sensor 64 is typically implemented by a conventional resistance temperature device (RTD) sensor, and is disposed on the basin floor exterior surface within the confines of the heating pad to sense the temperature of liquid disposed in basin 32 as described above. Thermostat 62 and temperature sensor 64 may be disposed anywhere on the basin floor exterior surface (e.g., except on the heating pad) capable of controlling the heating pad. A connector 68 is disposed within heating pad 70 for facilitating connections to enable temperature controller 38, thermostat 62 and temperature sensor 64 to control the heating pad as described above. Connector 68 may be implemented by any conventional or other type of connector and may be disposed anywhere on the heating pad. Heating pad 70 applies thermal energy to the basin floor periphery to heat liquid and other objects placed within the basin, while remaining portions of the basin not coincident the heating pad absorb thermal energy from the heating pad. Since the basin floor absorbs thermal energy from the heating pad, the drape is prevented from absorbing excess thermal energy that may burn and/or melt the drape when objects are placed within the basin.

A surgical drape disposed over a thermal treatment system having warming basin 32 of FIG. 6 and receiving an object within the basin is illustrated in FIG. 7. Specifically, a thermal treatment system 3c is substantially similar to system 3a described above for FIG. 2 except that system 3c includes basin 32 having heating pad 70 arranged in a generally annular configuration. System 3c heats liquid within basin 32 in substantially the same manner described above for FIG. 4, while drape 17 is substantially similar to the drape described above for FIG. 1. In operation, drape 17 is disposed over thermal treatment system 3c and within basin 32 to form a drape receptacle within the basin for containing a heated sterile liquid as described above. By way of example only, a pitcher 14, commonly referred to as a graduate and typically containing an antibiotic or other solution, is placed on drape 17 within basin 32 to heat solution residing in the pitcher. Pitcher 14 may be placed on the basin floor either within the confines of heating pad 70, or with a small portion of the pitcher disposed coincident the heating pad. Heating pad 70 applies thermal energy to the basin floor periphery to heat the sterile liquid and pitcher, while remaining portions of the basin floor (e.g., basin floor portions not coincident the heating pad) absorb thermal energy from the heating pad. The absorption of thermal energy by the basin prevents the drape from absorbing excess amounts of thermal energy sufficient to burn and/or melt the drape, thereby protecting the drape from damage and ensuring sterility of the sterile liquid. Various other objects (e.g., medical instruments, containers, etc.) may be placed within the basin to be heated by the basin and sterile liquid in substantially the same manner described above.

Figure 8:
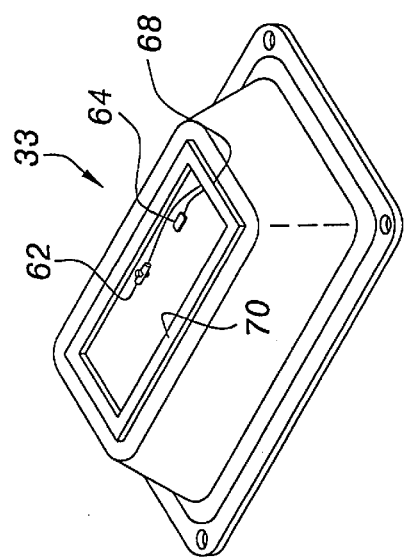
FIG. 8 is a view in perspective of a substantially rectangular thermal treatment system warming basin including a substantially rectangular heating pad extending about the basin floor toward the basin floor periphery according to the present invention.

A substantially rectangular warming basin having a heating pad disposed about the basin floor exterior surface toward the basin floor periphery to enable the basin to absorb thermal energy that may otherwise damage a surgical drape when objects are placed in that basin is illustrated in FIG. 8. Warming basin 33 is substantially similar to the substantially rectangular warming basin described above for FIG. 3, and is illustrated in FIG. 8 in an inverted position relative to use within a thermal treatment system for descriptive purposes. However, the basin is mounted within a thermal treatment system in substantially the same manner illustrated in FIG. 9. Specifically, basin 33 includes a heating pad 70, a thermostat 62 and a temperature sensor 64, each disposed on the basin floor exterior surface. Heating pad 70 is substantially similar to the heating pad described above for FIG. 6 except that the heating pad utilized with basin 33 is arranged in a generally rectangular configuration. In particular, the heating pad is in the form of a generally rectangular loop having an open interior portion, and is disposed about the basin floor exterior surface toward the basin floor periphery (e.g., toward the junction between the basin side and bottom walls). By way of example only, the rectangular loop configuration of the heating pad includes a length extending along the longer dimension basin floor edges of approximately ten inches and a width extending along the shorter dimension basin floor edges of approximately four inches. The open interior portion of the heating pad configuration includes a length extending along the longer dimension basin floor edges of approximately eight inches and a width extending along the shorter dimension basin floor edges of approximately two inches, thereby providing a heating pad thickness (e.g., the thickness of the heating pad arranged in the generally rectangular loop configuration) of approximately one inch.

Thermostat 62 and temperature sensor 64 are substantially similar to the thermostat and temperature sensor described above for FIG. 6, and function along with temperature/indicator 38 (FIG. 9) to control heating pad 70 to heat sterile liquid contained within basin 33 in substantially the same manner described above for FIGS. 6–7. Thermostat 62 and temperature sensor 64 are disposed on the basin floor exterior surface adjacent each other within the confines of the heating pad interior portion toward a longer dimension basin floor edge (e.g., the topmost basin floor edge as viewed in FIG. 8). However, the thermostat and temperature sensor may be disposed anywhere on the basin floor exterior surface (e.g., except on the heating pad) capable of controlling the heating pad. A connector 68, substantially similar to the connector described above for FIG. 6, is disposed within heating pad 70 toward a shorter dimension basin floor edge (e.g., the rightmost basin floor edge as viewed in FIG. 8) for facilitating connections to enable temperature controller/ indicator 38, thermostat 62 and temperature sensor 64 to control heating pad 70 as described above. Heating pad 70 applies thermal energy to the basin floor periphery to heat liquid and other objects placed within the basin, while remaining portions of the basin not coincident the heating pad absorb thermal energy from the heating pad. Since the basin floor absorbs thermal energy from the heating pad, the drape is prevented from absorbing excess thermal energy that may burn and/or melt the drape when objects are placed within the basin.

Figure 9:
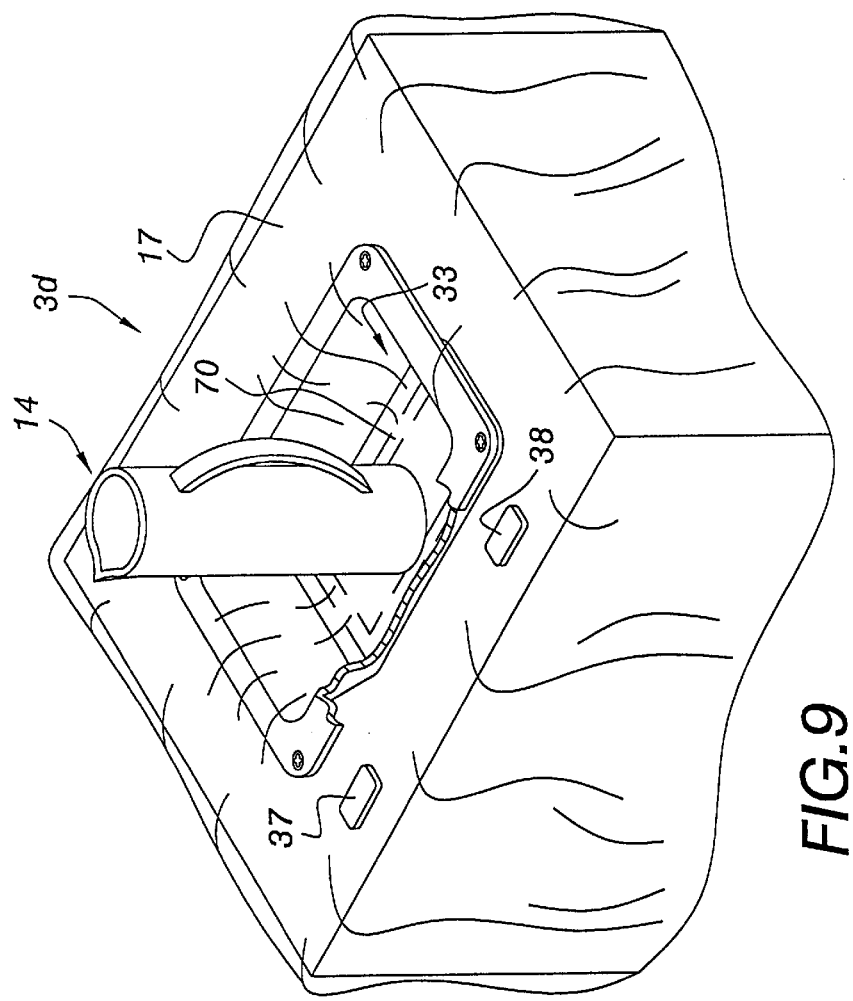
FIG. 9 is a view in perspective of an object placed on a surgical drape disposed over a thermal treatment system having the substantially rectangular basin of FIG. 8.

A surgical drape disposed over a thermal treatment system having basin 33 of FIG. 8 and receiving an object within the basin is illustrated in FIG. 9. Specifically, drape 17 and thermal treatment system 3d are substantially similar to the drape and system 3c described above for FIG. 7 except that system 3d includes substantially rectangular basin 33 having heating pad 70 arranged in the generally rectangular configuration described above. In operation, drape 17 is disposed over thermal treatment system 3d and within basin 33 to form a drape receptacle within the basin for containing a heated sterile liquid as described above. By way of example only, a pitcher 14, commonly containing an antibiotic or other solution, is placed on drape 17 within basin 33 to heat liquid residing in the pitcher. Pitcher 14 may be placed on the basin floor either within the confines of the heating pad interior portion, or with a small portion of the pitcher coincident the heating pad. Heating pad 70 applies thermal energy to the basin floor periphery to heat the sterile liquid and pitcher, while remaining portions of the basin floor (e.g., basin floor portions not coincident the heating pad) absorb thermal energy from the heating pad. The absorption of thermal energy by the basin prevents the drape from absorbing excess amounts of thermal energy sufficient to burn and/or melt the drape, thereby protecting the drape from damage and ensuring sterility of the sterile liquid. Various other objects (e.g., medical instruments, containers, etc.) may be placed within the basin to be heated by the basin and sterile liquid in substantially the same manner described above.

The heating pad may be disposed on the exterior surface of a thermal treatment system basin floor in various configurations (e.g., spiral configurations, 'X' or 'I' configurations, serpentine, tortuous or zigzag configurations, or other configurations) that cover a portion of the basin floor. Since a drape is disposed over a thermal treatment system and within a basin, these heating pad configurations prevent damage to the drape from absorption of excess thermal energy when objects are placed in the basin as described above. The particular heating pad configuration utilized for a basin may depend upon the quantity and size of objects placed in that basin. For example, heating pad configurations covering relatively small portions of the basin floor are utilized where large objects and/or substantial quantities of objects are to be placed in the basin since, in these instances, the basin is required to absorb a fair amount of thermal energy to prevent damage to the drape. Conversely, heating pad configurations covering substantial portions of the basin floor are typically utilized where small objects and/or lesser quantities of objects are to be placed within the basin since, in these instances, the basin is required to absorb lesser amounts of thermal energy to prevent damage to the drape.

Although the generally annular and rectangular heating pad configurations respectively described above for FIGS. 6 and 8 are preferred, several other heating pad configurations are illustrated, by way of example only, in FIGS. 10–24. These alternative heating pad configurations are illustrated and described below with reference to substantially rectangular basin 33 described above, however, the heating pad configurations may be disposed in any fashion on any shaped basin. Further, the heating pad configurations may be disposed on the basin floor via the fastening techniques described above, and include the necessary wiring and components (not shown, e.g., the temperature controller/ indicator, thermostat and temperature sensor) described above to heat sterile liquid contained within the basin. Moreover, basin 33 having any of the heating pad configurations described below is utilized within a thermal treatment system and heats liquid contained within the basin in substantially the same manner described above for FIGS. 8–9.

Referring to FIGS. 10 and 11, heating pad 70 may be configured in a serpentine, tortuous or zigzag manner and extend across the floor of basin 33. A serpentine configuration of the heating pad may include a plurality of substantially rectangular segment portions 50 (FIG. 10) successively connected to each other toward their shorter dimension edges. Adjoining segment portions are connected at opposing angles to form jagged or sharp windings as the heating pad extends in the direction of a longitudinal axis of the basin floor. The adjoining segment portions may interface at any suitable opposing angles, while the serpentine heating pad is typically disposed on the basin floor toward the approximate center between the longer dimension basin floor edges. Segment portions 50 may be of any quantity, shape or size, may be disposed on the basin floor exterior surface in any fashion, and may be implemented by individual units or be combined within a single unit to form the heating pad configuration described above.

Further, a serpentine heating pad configuration may include a plurality of generally rectangular elongated segment portions 47 (FIG. 11) successively connected to each other toward their shorter dimension edges. Adjoining segment portions smoothly interface to form curved windings (e.g., the configuration resembles a backwards 'N') as the heating pad extends in the direction of a transverse axis of the basin floor. Elongated segment portions 47 may be of any quantity, shape or size, may be disposed on the basin floor exterior surface in any fashion, and may be implemented by individual units or be combined into a single unit to form the heating pad configuration described above.

Alternatively, heating pad 70 may cover substantially the entire basin floor with an opening defined in the heating pad in a serpentine configuration to permit the basin floor to absorb thermal energy and prevent drape damage as described above. The serpentine configuration for the opening may include jagged or sharp windings (FIG. 12) or smooth curving windings (FIG. 13) substantially similar in configuration to the heating pads respectively described above for FIGS. 10 and 11.

Referring to FIGS. 14–16, heating pad 70 may include a plurality of heating segments 52, 54 (FIG. 14). Segments 54 are generally semi-elliptical with their major axes extending in a direction of a basin floor transverse axis, and are typically disposed toward opposing shorter dimension edges of the basin floor. Segments 52 are substantially rectangular with the longer segment dimension extending in a direction of the basin floor transverse axis, and are disposed between segments 54. Segments 52, 54 are typically aligned along a basin floor longitudinal axis and are spaced apart by a slight distance to enable these segments to be disposed across the basin floor in a direction of that longitudinal axis. However, segments 52, 54 may be of any quantity, shape or size, and may be disposed on the basin floor exterior surface in any fashion.

Similarly, heating pad 70 may include a plurality of elongated heating strips 56 (FIG. 15). Strips 56 are generally rectangular or elliptical and extend across the basin floor substantially in parallel with their major axes or longer rectangular dimension extending in a direction of the basin floor longitudinal axis. Strips 56 are aligned along a basin floor transverse axis and are spaced apart by a slight distance to enable the strips to be disposed across the basin floor in a direction of the basin floor transverse axis. The heating strips may be of any quantity, shape or size, and may be disposed on the basin floor exterior surface in any fashion. Moreover, heating pad 70 may include a single elongated strip portion 58 having a plurality of projections 59 extending from the strip portion (FIG. 16). Strip portion 58 is generally rectangular with its longer dimension extending in a direction of a basin floor longitudinal axis. Projections 59 transversely extend from strip portion 58 substantially in parallel, and are separated by a slight distance along strip portion 58 to cover portions of the basin floor. The projections are generally rectangular and taper toward their distal ends to form a rounded peak. The lengths or distance projections 59 transversely extend from strip portion 58 successively increase or decrease as the projections extend from sequential locations along the strip portion. Strip portion 58 may be of any shape or size, while projections 59 may be of any quantity, shape or size and extend in any fashion from the strip portion. The strip portion and projections may be disposed on the basin floor exterior surface in any fashion, and may be implemented by individual units or be combined into a single unit to form the heating pad configuration described above.

Alternatively, heating pad 70 may cover substantially the entire basin floor with openings defined in the heating pad to permit the basin floor to absorb thermal energy to prevent drape damage as described above. The heating pad openings may be in the form of segment portions 52, 54 (FIG. 17), elongated heating strips 56 (FIG. 18) or strip portion 58 and projections 59 (FIG. 19) substantially similar in configuration to the heating pads respectively described above for FIGS. 14–16.

Referring to FIGS. 20–22, heating pad 70 may be configured into a plurality of heating segments 51 (FIG. 20). The heating segments are substantially rectangular with their longer dimension extending in a direction of a basin floor transverse axis. Segments 51 are aligned along a basin floor longitudinal axis and spaced apart by a slight distance to enable the segments to be disposed across the basin floor in a direction of the basin floor longitudinal axis. Segments 51 may be of any quantity, shape or size, and may be disposed on the basin floor exterior surface in any fashion. Further, heating pad 70 may be configured in the form of a generally rectangular loop 53 (FIG. 21) having rounded corners and an open interior portion. The heating pad is typically disposed about the basin floor exterior surface toward the basin floor periphery, and may be of any shape or size. In addition, heating segments 51 may be disposed within the open interior portion of loop 53 to provide a combined configuration (FIG. 22).

Heating pad 70 may further be configured to cover substantially the entire basin floor and include an opening 55 (FIG. 23) defined toward the center of the heating pad. Opening 55 is typically substantially circular and includes dimensions sufficient to accommodate a pitcher or other object placed within the basin, but may be of any size or shape. Further, the basin may include indicia directing placement of the pitcher or other object within the basin coincident opening 55 to prevent damage to the drape from absorption of excess thermal energy as described above.

Referring to FIG. 24, heating pad 70 is configured in an additional manner to heat a portion of a basin floor. Specifically, heating pad 70 includes a heating element 57 and covers substantially the entire basin floor. Heating element 57 is disposed within heating pad 70 and is configured to cover and apply thermal energy to a portion of the basin floor. The heating element includes heating element segments 49 having curved portions at their proximal ends. The heating element segments are connected at their proximal ends and initially curve away from each other to extend substantially in parallel, separated by a relatively constant distance, toward their distal ends. In other words, the heating element segments are connected to form a generally 'U' shaped configuration. The heating element may be of any size or shape, may be arranged in any configuration that covers a portion of the basin floor, and may be disposed in any manner within the heating pad, while the heating pad may be disposed on the basin floor exterior surface in any fashion.

The various heating pad configurations described above may be utilized with any shaped basin, and may be utilized with warming basins contained in single (e.g., FIGS. 2 and 3) or multiple basin (e.g., FIG. 5) thermal treatment systems in substantially the same manner described above to prevent damage to drapes when objects are placed in those warming basins. It is to be understood that the heating pads and heating element described above may be disposed on a basin in any fashion, and may be of any configuration that covers a portion of the basin floor to enable the basin to absorb thermal energy and prevent damage to the drape as described above.

Figure 25:
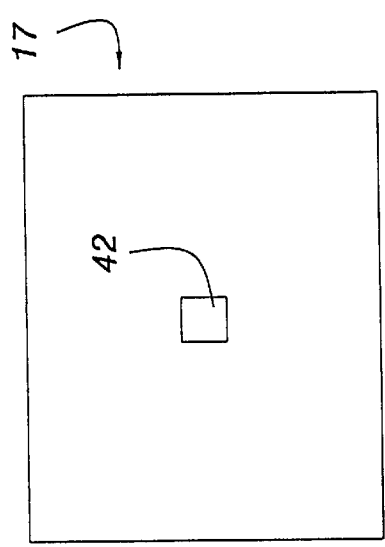
FIG. 25 is a top view in plan of a surgical drape having reflective material disposed at the approximate center of the drape for reflecting infrared light from an infrared light source toward an infrared detector disposed below a thermal treatment system basin to indicate the proper positioning and/or presence of the drape on a thermal treatment system according to the present invention.

Generally, a surgical drape is disposed over a thermal treatment system and within each thermal treatment system basin to provide a sterile field above each basin to maintain sterility of a sterile liquid or medium. However, use of the thermal treatment system without the drape or with the drape improperly positioned may compromise sterility of the sterile liquid and an entire surgical procedure. A surgical drape for use with a thermal treatment system that utilizes infrared light to detect the proper positioning and/or presence of the drape on the thermal treatment system to ensure sterility of the sterile liquid is illustrated in FIG. 25. Specifically, drape 17 is substantially similar to the drape described above for FIG. 1 except that the drape includes a reflective material segment 42, preferably disposed at the approximate center of the non-sterile side of the drape. The reflective material segment may be constructed of any suitable reflective material, and may be disposed or affixed to the drape via any conventional adhesives or fastening techniques. Reflective material segment 42 is utilized to indicate the proper positioning and/or presence of the drape on the thermal treatment system as described below, and may further serve as centering or placement indicia to direct placement of the drape over the thermal treatment system. In particular, reflective material segment 42 may be disposed on the drape to indicate the center of a basin, while drape portions adjacent the segment are placed within that basin. The reflective material segment typically enables detection of drape presence, however, when the segment further functions as placement indicia, the presence and proper positioning of the drape on thermal treatment system may be detected as described below. The reflective material segment may further include or be masked by a bar code indicating the drape type. Since certain drapes are compatible for use with particular thermal treatment systems, the bar code provides a manner to identify a drape compatible with a specific thermal treatment system. Users may manually examine the bar code or utilize a bar code system, similar to the system disclosed in the aforementioned Faries, Jr. et al U.S. Pat. No. (5,653,938), to determine drape compatibility with a thermal treatment system. Further, instructions relating to placement of the reflective segment and/or bar code on the system may be disposed on the reflective segment.

Drape 17 is placed over the thermal treatment system whereby a portion of the drape is pushed down into and conforms to a thermal treatment system basin to form a drape receptacle as described above with reflective material segment 42 disposed at the center of the basin floor coincident an infrared light source or emitter and corresponding detector embedded within the thermal treatment system below the basin as described below. Infrared light emitted from the light source is reflected by reflective material segment 42 and sensed by the detector to indicate the proper positioning and/or presence of the drape on the thermal treatment system and to enable thermal treatment system operation as described below. Reflective material segment 42 may be of any size or shape, and may be disposed integral with or attached to the drape at any location capable of reflecting light from the infrared light source toward the detector.

Figure 27:
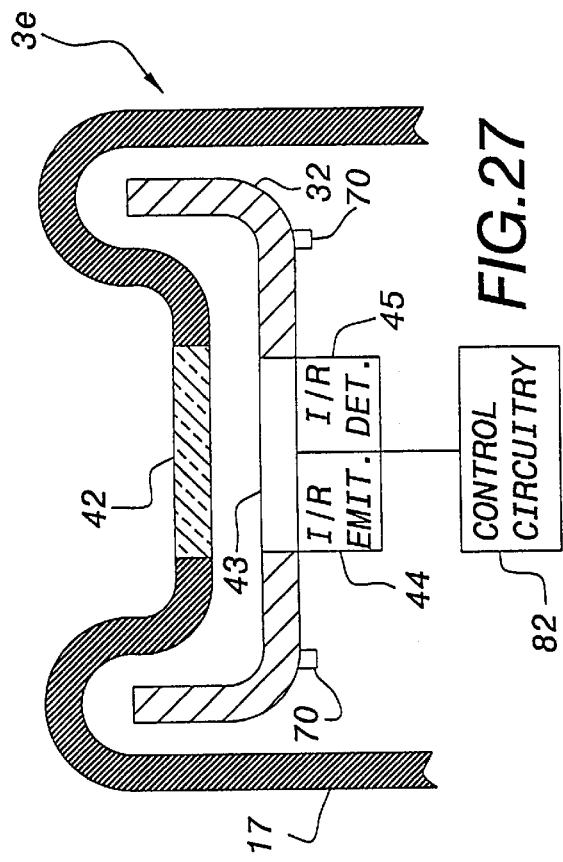
FIG. 27 is a side view in elevation and partial section of the thermal treatment system of FIG. 26 schematically illustrating the infrared light source and detector disposed below the thermal treatment system basin for detecting the proper positioning and/or presence of a drape placed on the thermal treatment system and enabling thermal treatment system operation.
Figure 26:
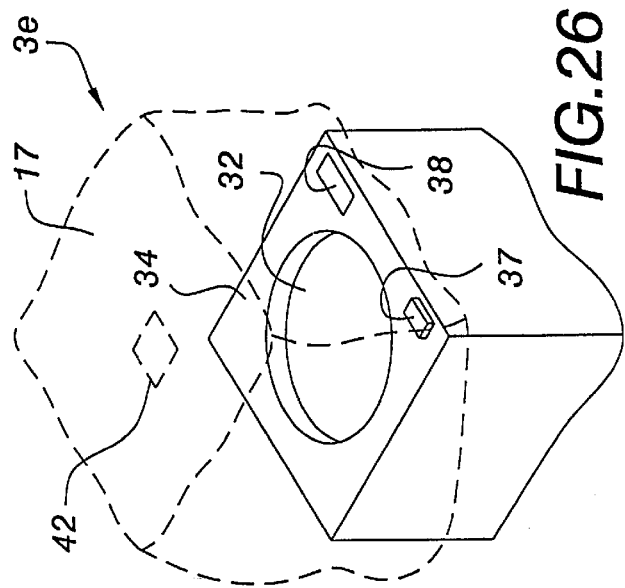
FIG. 26 is an exploded view in perspective of the surgical drape of FIG. 25 placed over a thermal treatment system including a warming basin having a generally annular heating pad configuration, and an infrared light source and detector embedded within the thermal treatment system below the basin for facilitating detection of infrared light reflected by the drape to verify the proper positioning and/or presence of the drape on the thermal treatment system and to enable thermal treatment system operation.

A thermal treatment system for utilizing the reflective drape and including a warming basin having a generally annular heating pad configuration is illustrated in FIGS. 26–27. Specifically, thermal treatment system 3e is substantially similar to thermal treatment system 3c described above except that the system 3e includes an infrared light source 44 and a corresponding detector 45 configured to sense the infrared light emitted from the infrared light source. Infrared light source 44 and detector 45 are typically embedded adjacent each other within the thermal treatment system below basin 32, however, the infrared light source and detector may be disposed anywhere on the thermal treatment system capable of detecting the proper positioning and/or presence of the drape. Basin 32 is substantially similar to the warming basin described above for FIG. 6 except that basin 32 includes a window 43 disposed toward the approximate center of the basin floor to enable detector 45 to sense the drape. Heating pad 70 may be arranged in any heating pad configuration described above that may accommodate placement of window 43 and infrared light source 44 and detector 45 on or below the basin. Window 43 is typically implemented by a lens or glass cover, while infrared light source 44 and detector 45 are typically implemented by conventional infrared light sources and detectors, respectively.

When a drape is placed over thermal treatment system 3e with reflective material segment 42 disposed coincident light source 44 and detector 45, the infrared light source emits infrared light through window 43 toward reflective material segment 42, whereby the emitted infrared light is reflected back from the reflective material segment through the window towards the infrared detector. Detector 45 generates signals in response to detecting infrared light that are transmitted to control circuitry 82 to indicate whether or not the drape is properly positioned and/or present on the thermal treatment system. When reflective material segment 42 serves as placement indicia, placement of the segment within the basin at a location detectable by detector 45 typically provides and enables the detector to sense proper drape positioning on the thermal treatment system. In response to receiving signals from detector 45 indicating the proper positioning and/or presence of the drape on the thermal treatment system, control circuitry 82 enables thermal treatment system operation. If detector 45 does not sense reflected infrared light, the drape is either absent from or improperly positioned on the thermal treatment system, and power is disabled to the system (e.g., temperature controller 38 does not receive power), except that a light disposed within power switch 37 remains illuminated. Thermal treatment system 3e typically functions to continuously monitor the drape and disable power to the temperature controller when the drape is no longer detected (e.g., the drape shifts position or is removed during system operation). However, conventional interlock circuitry may be provided to maintain power to the temperature controller after initial detection of a drape until the thermal treatment system is powered down.

Figure 28:
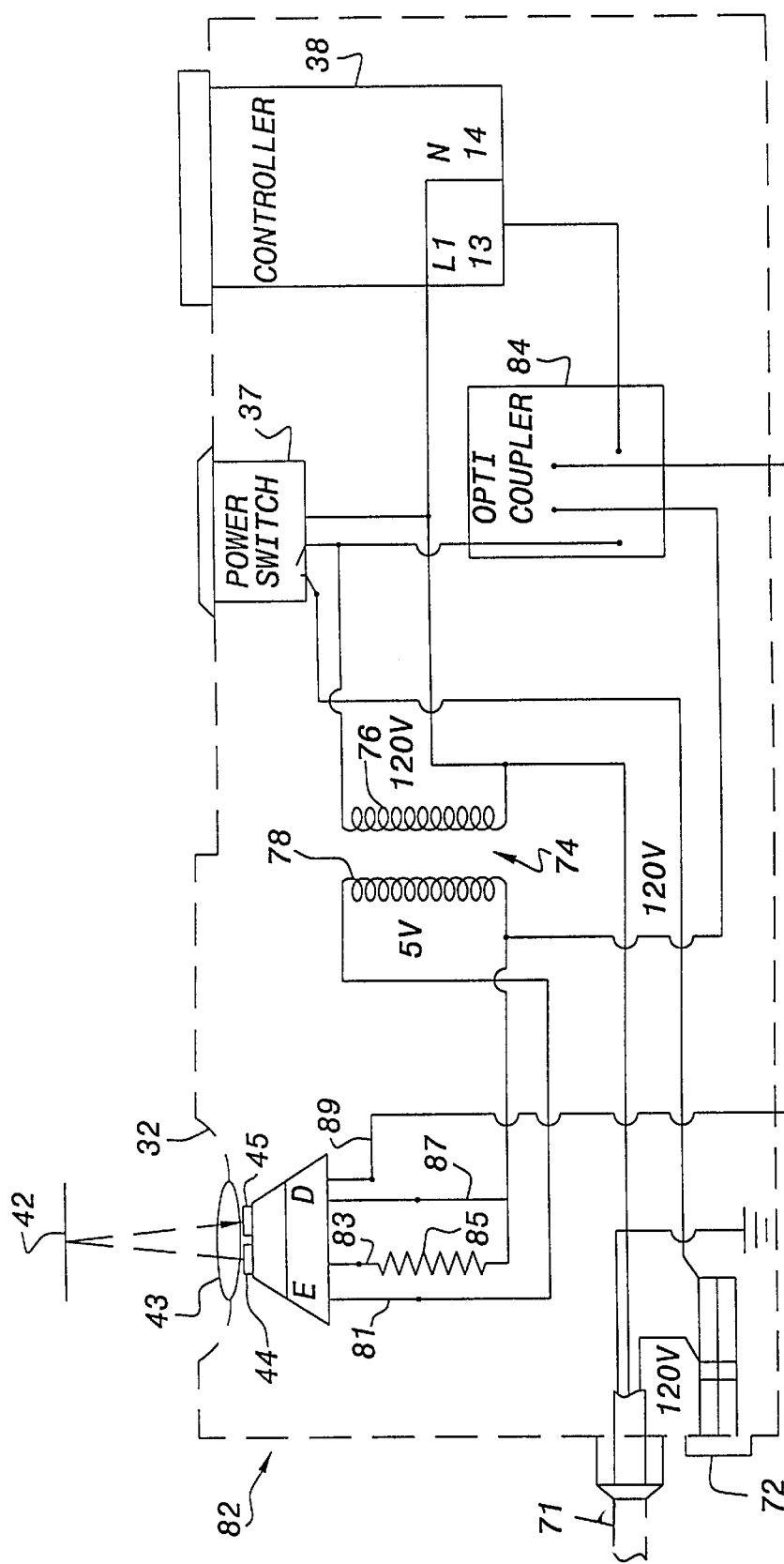
FIG. 28 is an electrical schematic of an exemplary control circuit of the thermal treatment system of FIG. 27 for sensing the proper positioning and/or presence of a drape placed on the thermal treatment system via the infrared light source and detector, and enabling thermal treatment system operation.

An exemplary control circuit for receiving signals from detector 45 and initiating thermal treatment system operation in response to detecting the proper positioning and/or presence of a drape on the thermal treatment system is illustrated in FIG. 28. Specifically, control circuitry 82 is embedded within thermal treatment system 3e (FIG. 27) with infrared light source 44 and detector 45 positioned proximate window 43 of basin 32 to detect reflected infrared light from reflective material segment 42 as described above. Control circuitry 82 includes a power cord 71 that extends from the circuit to a common wall outlet jack to provide power, typically 120V, to the system. The power cord is connected in series with a fuse 72 that disables connections in response to voltage and/or current exceeding a threshold. A heater power switch 37, typically including a light and being substantially similar to the power switch described above, is connected in series with fuse 72 and enables power to a D.C. power supply or transformer 74, and an opticoupler or solid state relay 84. Transformer 74 typically includes primary and secondary windings 76, 78 and converts power from power cord 71 to 5V D.C. for use by infrared light source 44 and detector 45. Primary winding 76 receives power, typically 120V, via power switch 37 and enables 5V D.C. to be present on secondary winding 78. Infrared light source 44 is connected in series to secondary winding 78 via lines 81, 83 to receive power to emit infrared light. Line 83 includes a resistor 85 disposed between light source 44 and secondary winding 78 to regulate current. The resistor may include any suitable resistance to achieve a desired current and/or voltage along line 83. Detector 45 is connected to secondary winding 78 via a line 87, and is also connected to opticoupler 84 via a line 89. Line 89 typically contains signals indicating the presence or absence of reflected infrared light, and hence, the proper positioning and/or presence of the drape on the thermal treatment system. Opticoupler 84 is coupled to power switch 37, detector 45, secondary winding 78 and a temperature controller/indicator 38. The opticoupler receives signals from detector 45 and enables power to temperature controller/indicator 38 in response to signals indicating the proper positioning and/or presence the drape on the thermal treatment system. Temperature controller/indicator 38 is substantially similar to the temperature controller/indicator described above, and is connected to power cord 71 and opticoupler 84 whereby the opticoupler controls power to the temperature controller based on signals received from detector 45 as described above.

Operation of thermal treatment system 3e is described with reference to FIGS. 25–28. Initially, drape 17 is placed over thermal treatment system 3e with reflective material segment 42 disposed at the approximate center of the basin floor coincident window 43 and infrared light source 44 and detector 45 as described above. Power switch 37 is activated whereby infrared light source 44 emits light through window 43 toward reflective material segment 42. The emitted infrared light is reflected from reflective material segment 42 back through the window toward detector 45. Detector 45 receives the infrared light reflected from reflective material segment 42 and generates and transmits signals indicating the proper positioning and/or presence of the drape on the thermal treatment system to opticoupler 84 of control circuitry 82. The opticoupler enables power to temperature controller 38 to permit thermal treatment of basin 32. When drape 17 is absent from or improperly positioned on the thermal treatment system, infrared light emitted from light source 44 is not reflected toward detector 45, whereby detector 45 does not detect infrared light. Opticoupler 84 receives signals from detector 45 indicating absence or improper positioning of the drape on the thermal treatment system and does not enable or, in other words, disables power to temperature controller 38 to cease or prevent thermal treatment of basin 32. However, power switch 37 remains illuminated even after disablement of power to the temperature controller. The drape may include any quantity of reflective material segments. (e.g., at least one), while the system may include any quantity of infrared or other light sources and detectors (e.g., at least one) disposed about the system to detect the proper positioning and/or presence of the drape in substantially the same manner described above whereby the detector outputs may be combined in any manner (e.g., AND, OR, etc.) to verify the proper positioning and/or presence of the drape on the thermal treatment system. Further, the light source and detector may utilize any frequency or band of light to detect proper positioning and/or presence of the drape in substantially the same manner described above.

Figure 29:
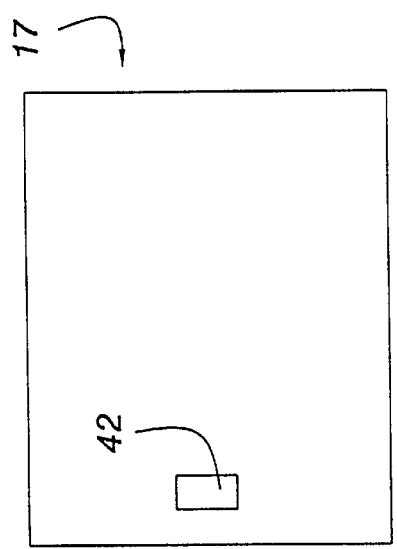
FIG. 29 is a top view in plan of a surgical drape having reflective material disposed toward a drape edge for reflecting infrared light emitted from an infrared light source toward a detector disposed within a thermal treatment system top surface to indicate the proper positioning and/or presence of the drape on a thermal treatment system according to the present invention.

An alternative embodiment for a surgical drape for use with a thermal treatment system that utilizes infrared light to detect the proper positioning and/or presence of the drape on the thermal treatment system is illustrated in FIG. 29. Specifically, drape 17 is substantially similar to the drape described above for FIG. 25 except that reflective material segment 42 is preferably disposed on the non-sterile side of the drape toward a drape edge (e.g., the leftmost edge as viewed in FIG. 29). Reflective material segment 42 is utilized to indicate the proper positioning and/or presence of the drape on the thermal treatment system in a similar manner as described above, and may further serve as placement indicia to direct placement of the drape over the thermal treatment system. In particular, reflective material segment 42 may be disposed on the drape such that drape portions adequately cover and provide a sterile field for the thermal treatment system when the reflective material segment is placed coincident an infrared light source and detector embedded within a thermal treatment system top surface. The reflective material segment typically enables detection of drape presence, however, when the segment further functions as placement indicia, the presence and proper positioning of the drape on thermal treatment system may be detected as described below. Reflective material segment 42 may be disposed or affixed to the drape via any conventional adhesives or fastening techniques described above, and may further include or be masked by a bar code to determine drape compatibility with the thermal treatment system as described above. Moreover, instructions relating to placement of the reflective material segment and/or bar code on the thermal treatment system may be disposed on the reflective material segment.

Drape 17 is placed over the thermal treatment system whereby a portion of the drape is pushed down into and conforms to the basin to form a drape receptacle as described above with reflective material segment 42 disposed coincident an infrared light source and detector embedded within the top surface of the thermal treatment system. Infrared light emitted from the light source is reflected by reflective material segment 42 and sensed by the detector to indicate the proper positioning and/or presence of the drape on the thermal treatment system and to enable thermal treatment system operation as described above. Reflective material segment 42 may be of any size or shape, and may be disposed integral with or attached to the drape at any location capable of reflecting light from the infrared light source toward the detector.

Figure 31:
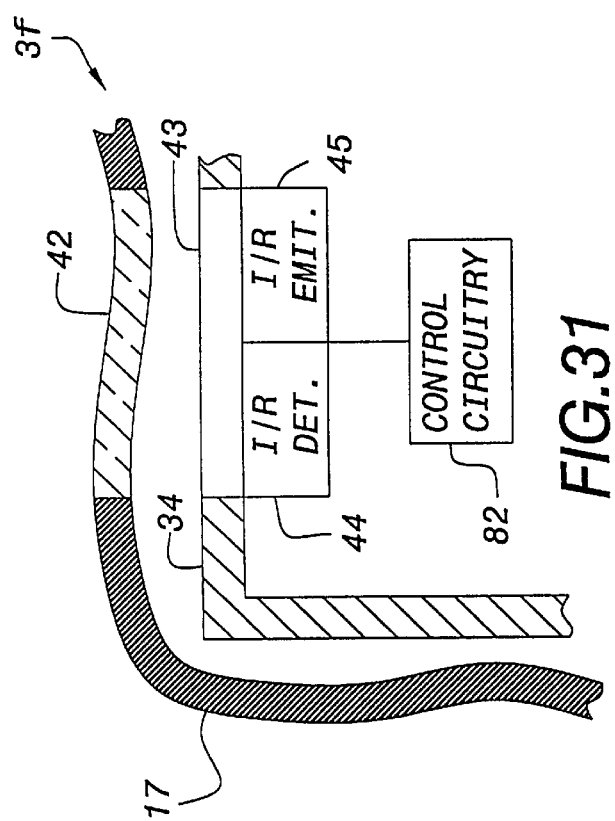
FIG. 31 is a side view in elevation and partial section of the thermal treatment system of FIG. 30 schematically illustrating the infrared light source and detector disposed within a thermal treatment system top surface for detecting the proper positioning and/or presence of the drape on the thermal treatment system and enabling thermal treatment system operation.
Figure 30:
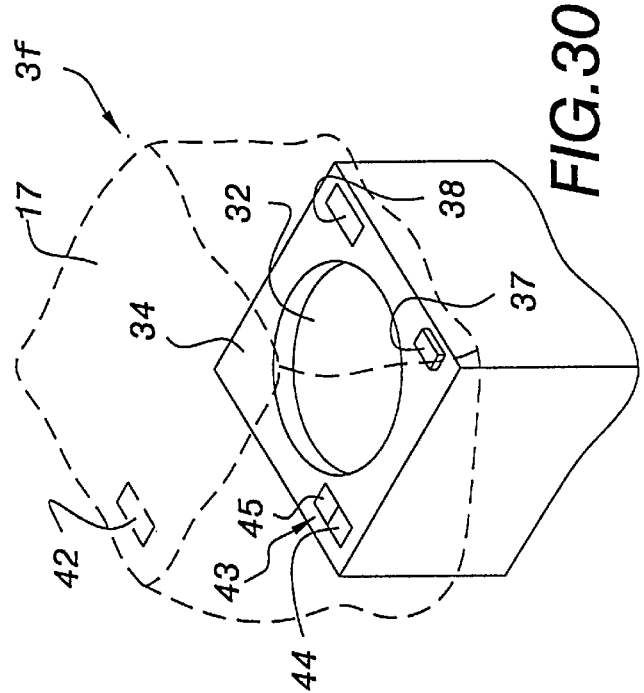
FIG. 30 is an exploded view in perspective of the surgical drape of FIG. 29 placed over a thermal treatment system including a warming basin having a generally annular heating pad configuration, and an infrared light source and detector embedded within a thermal treatment system top surface for facilitating detection of infrared light reflected by the drape to verify the proper positioning and/or presence of the drape on the thermal treatment system and to enable thermal treatment system operation.

A thermal treatment system including a warming basin having a generally annular heating pad configuration, and an infrared light source and detector disposed in a thermal treatment system top surface to detect proper positioning and/or presence of a drape on the thermal treatment system is illustrated in FIGS. 30–31. Specifically, thermal treatment system 3f is substantially similar to and functions in substantially the same manner as system 3e described above except that the infrared light source and detector are embedded within a thermal treatment system top surface 34. Top surface 34 includes a window 43, typically implemented by a lens or glass cover as described above, wherein the infrared light source and detector are disposed adjacent each other below the window. However, the infrared light source, detector and window may be disposed anywhere on the thermal treatment system capable of detecting the proper positioning and/or presence of the drape. Basin 32 is substantially similar to the basin described above for FIG. 6, while heating pad 70 may be arranged in any heating pad configuration described above. When drape 17 is placed over thermal treatment system 3f with reflective material segment 42 disposed coincident light source 44 and detector 45, the infrared light source emits infrared light through window 43 toward reflective material segment 42 whereby the emitted light is reflected back from the reflective material segment through the window towards the detector. Detector 45 generates signals in response to detecting infrared light that are transmitted to control circuitry 82 to indicate whether or not the drape is properly positioned and/or present on the thermal treatment system. Control circuitry 82 is substantially similar to the control circuitry described above for FIG. 28 except that the light source and detector are disposed within the thermal treatment system top surface. When reflective material segment 42 serves as placement indicia, placement of the reflective material segment on the thermal treatment system top surface at a location detectable by detector 45 typically provides and enables the detector to sense proper drape positioning on the thermal treatment system. In response to receiving signals from detector 45 indicating the proper positioning and/or presence of the drape on the thermal treatment system, control circuitry 82 enables thermal treatment system operation in substantially the same manner described above. If detector 45 does not sense reflected infrared light, the drape is either absent from or improperly positioned on the thermal treatment system, and power is disabled to the system (e.g., temperature controller 38 does not receive power) as described above, except that power switch 37 remains illuminated. Further, thermal treatment system 3f typically functions to continuously monitor the drape and disable power to the temperature controller when the drape is no longer detected (e.g., the drape shifts position or is removed during system operation). However, conventional interlock circuitry may be provided as described above to maintain power to the temperature controller after initial detection of a drape until the thermal treatment system is powered down.

The infrared drape detection techniques described above may be utilized with cooling and/or warming basins of any single or multiple basin thermal treatment systems in substantially the same manner described above. The basin window and infrared light source and detector may be disposed at any appropriate locations to accommodate warming basin heating pads and cooling basin dislodgement mechanisms. In addition, a bar code system, such as the system disclosed in the aforementioned Faries, Jr. et al U.S. Pat. No. (5,653,938), may be disposed beneath the basin adjacent the basin window or at any other location on the thermal treatment system to detect and/or process bar codes attached to drapes to determine drape sterility, compatibility or other drape characteristics in substantially the same manner described in that Faries, Jr. et al patent.

Figure 32:
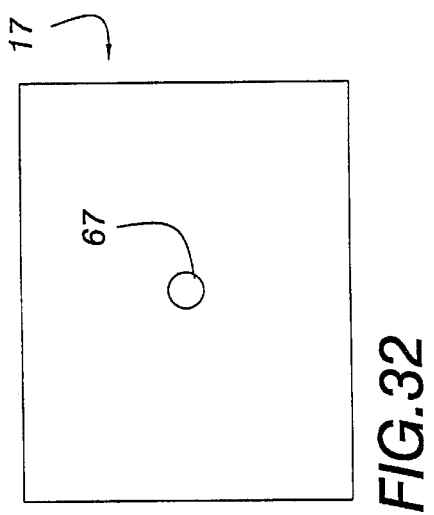
FIG. 32 is a top view in plan of a surgical drape having magnetic media disposed at the approximate center of the drape for detection by a magnetic detector disposed below a thermal treatment system basin to indicate the proper positioning and/or presence of the drape on a thermal treatment system according to the present invention.

The proper positioning and/or presence of a drape placed on a thermal treatment system may also be detected by utilizing a drape including magnetic media as illustrated in FIG. 32. Specifically, drape 17 is substantially similar to the drape described above for FIG. 25 except that drape 17 includes magnetic media 67 disposed within the drape or on the sterile or non-sterile surface of the drape. Magnetic media 67 may be any conventional magnetic media formed into any quantity of strips or other shapes (e.g., at least one), and disposed on or within the drape in any fashion that enables detection of the media via any conventional or other fastening techniques. By way of example only, magnetic media 67 are in the form of a magnetic segment disposed toward the center of the drape. Magnetic media 67 are utilized to indicate the proper positioning and/or presence of the drape on the thermal treatment system as described below, and may further serve as centering or placement indicia to direct placement of the drape over the thermal treatment system. In particular, magnetic media 67 may be disposed on the drape to indicate the center of a basin, while drape portions adjacent the magnetic media are placed within that basin. Magnetic media 67 typically enable detection of drape presence, however, when the magnetic media further function as placement indicia, the presence and proper positioning of the drape on thermal treatment system may be detected as described below. Further, the magnetic media may include or be masked by a bar code to determine drape compatibility with thermal treatment systems as described above whereby instructions relating to placement of the magnetic media and/or bar code may be disposed on the magnetic media.

Drape 17 is placed over the thermal treatment system whereby a portion of the drape is pushed down into and conforms to the basin to form a drape receptacle as described above with magnetic media 67 disposed coincident a magnetic detector embedded on an exterior surface of the thermal treatment system basin as described below. The magnetic detector senses magnetic media 67 to indicate the proper positioning and/or presence of the drape on the thermal treatment system and to enable thermal treatment system operation as described below.

Figure 34:
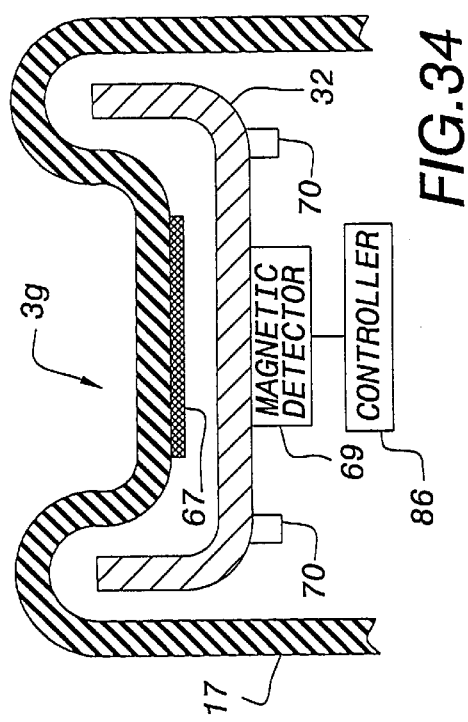
FIG. 34 is a side view in elevation and partial section of the thermal treatment system of FIG. 33 schematically illustrating the magnetic detector disposed below a thermal treatment system basin for detecting the proper positioning and/or presence of a drape placed on the thermal treatment system and enabling thermal treatment system operation.
Figure 33:
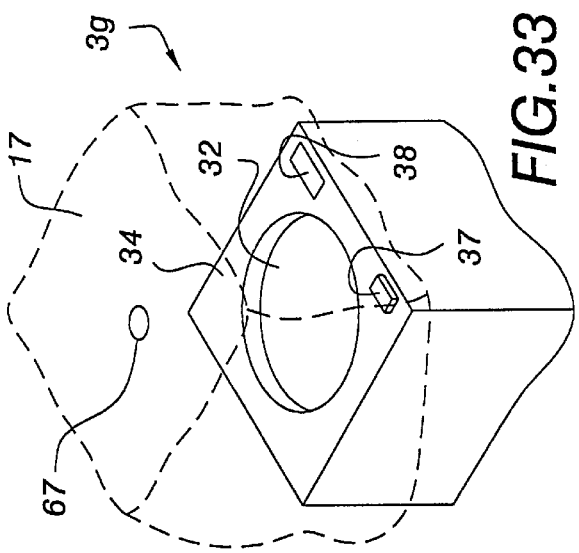
FIG. 33 is an exploded view in perspective of the surgical drape of FIG. 32 placed over a thermal treatment system including a warming basin having a generally annular heating pad configuration, and a magnetic detector embedded within the thermal treatment system below the basin for detecting the drape magnetic media to verify the proper positioning and/or presence of the drape on the thermal treatment system and to enable thermal treatment system operation.

A thermal treatment system for utilizing the magnetic drape and including a warming basin having a generally annular heating pad configuration is illustrated in FIGS. 33–34. Specifically, thermal treatment system 3g is substantially similar to system 3a described above except that system 3g includes a magnetic detector 69 disposed toward the center of an exterior surface of the thermal treatment system basin. Magnetic detector 69 is typically implemented by a conventional magnetic detector, preferably in the form of a magnetic tape sensor patch that adheres to the bottom center of the basin and generates signals indicating detection of the magnetic media. However, the magnetic detector may be disposed anywhere on the basin capable of detecting the proper positioning and or presence of the drape. Basin 32 is substantially similar to the basin described above for FIG. 6, while heating pad 70 may be arranged in any configuration described above that may accommodate placement of magnetic detector 69 on the basin floor exterior surface. When drape 17 is placed over thermal treatment system 3g with magnetic media 67 disposed at a location detectable by magnetic detector 69, the magnetic detector generates signals in response to detecting the magnetic media. The signals are transmitted to a controller 86, typically implemented by a conventional controller or microprocessor embedded within the thermal treatment system, to indicate whether or not the drape is properly positioned and/or present on the thermal treatment system. In response to receiving signals from detector 69 indicating the proper positioning and/or presence of the drape on the thermal treatment system, controller 86 enables thermal treatment system operation. When magnetic media 67 serve as placement indicia, placement of the magnetic media within the basin at a location detectable by magnetic detector 69 typically provides and enables the magnetic detector to sense proper drape positioning on the thermal treatment system. If magnetic detector 69 does not detect magnetic media 67, the drape is either absent or improperly positioned on the thermal treatment system and controller 86 does not enable or, in other words, disables power to temperature controller 38, while power switch 37 remains illuminated. Thermal treatment system 3g typically functions to continuously monitor the drape and disable power to the temperature controller when the drape is no longer detected (e.g., the drape shifts position or is removed during system operation). However, conventional interlock circuitry may be provided as described above to maintain power to the temperature controller after initial detection of a drape until the thermal treatment system is powered down.

In operation, drape 17 having magnetic media 67 is placed over thermal treatment system 3g with magnetic media 67 disposed coincident or at a location detectable by magnetic detector 69 disposed at the approximate center of the basin floor exterior surface. Power switch 37 is activated whereby magnetic detector 69 detects the presence of magnetic media 67. The magnetic detector generates and transmits signals, indicating that the drape is properly positioned and/or present on the thermal treatment system, to controller 86. Controller 86 receives the signals from magnetic detector 69 system and enables power to temperature controller 38 to permit thermal treatment of basin 32. When drape 17 is absent from or improperly positioned on the thermal treatment system, magnetic detector 69 does not detect magnetic media 67 and generates signals, indicating the absence or improper positioning of the drape, for transmission to controller 86. Controller 86, in response to receiving these signals from magnetic detector 69, does not enable or, in other words, disables power to temperature controller 38 to cease or prevent thermal treatment of basin 32, while power switch 37 remains illuminated. The drape may include any quantity of magnetic media disposed within or on the drape, while the thermal treatment system may include any quantity of associated detectors disposed within the thermal treatment system whereby the detectors may be disposed within the thermal treatment system in any manner capable of detecting the drape. The outputs of any quantity of magnetic detectors may be combined in any manner (e.g., AND, OR, etc.) to determine the proper positioning and/or presence of the drape on the thermal treatment system and enable system operation (e.g., any percentage of the detectors may be required to detect the drape to enable system operation). in addition, the drape may include a plurality of magnetic media for multiple basin thermal treatment systems wherein a magnetic detector is disposed below each basin to detect the proper positioning and/or presence of the drape as described above.

An alternative embodiment of a surgical drape for use with a thermal treatment system that utilizes magnetic media to detect the proper positioning and/or presence of the drape on a thermal treatment system is illustrated in FIG. 35. Specifically, drape 17 is substantially similar to the drape described above for FIG. 32 except that magnetic media 67 are in the form of a magnetic segment disposed within the drape or on the sterile or non-sterile surface of the drape toward a drape edge (e.g., the leftmost edge as viewed in FIG. 35). Magnetic media 67 are utilized to indicate the proper positioning and/or presence of the drape on the thermal treatment system in a similar manner as described above, and may further serve as placement indicia to direct placement of the drape over the thermal treatment system. In particular, magnetic media 67 may be disposed on the drape such that drape portions adequately cover and provide a sterile field for the thermal treatment system when the magnetic media are placed coincident a magnetic detector embedded within a thermal treatment system top surface. Magnetic media 67 typically enable detection of drape presence, however, when the magnetic media further function as placement indicia, the presence and proper positioning of the drape on thermal treatment system may be detected as described below. Magnetic media 67 may be disposed within or on the drape via any conventional adhesives or fastening techniques described above, and may further include or be masked by a bar code to determine drape compatibility with the thermal treatment system as described above. Moreover, instructions relating to placement of the magnetic media and/or bar code on the thermal treatment system may be disposed on the magnetic media.

Drape 17 is placed over the thermal treatment system whereby a portion of the drape is pushed down into and conforms to the basin to form a drape receptacle as described above with magnetic media 67 disposed coincident a magnetic detector embedded within the top surface of the thermal treatment as described below. The magnetic detector senses magnetic media 67 to indicate the proper positioning and/or presence of the drape on the thermal treatment system and enable thermal treatment operation as described below.

A thermal treatment system including a warming basin having a generally annular heating pad configuration, and a magnetic detector disposed within a thermal treatment system top surface to detect the proper positioning and/or presence of the drape on the thermal treatment system is illustrated in FIGS. 36–37. Specifically, thermal treatment system 3h is substantially similar to and functions in substantially the same manner as system 3g described above except that system 3h includes a magnetic detector 69 embedded within a top surface of the thermal treatment system. Top surface 34 typically includes a window 43 as described above wherein magnetic detector 69 is embedded within the top surface below the window to detect magnetic media 67 disposed on the drape. However, the magnetic detector may be disposed anywhere on the thermal treatment system capable of detecting the proper positioning and/or presence of the drape. Basin 32 is substantially similar to the basin described above for FIG. 6, while heating pad 70 may be arranged in any heating pad configuration described above.

When drape 17 is placed on thermal treatment system 3h with magnetic media 67 disposed coincident detector 69, the magnetic detector generates signals in response to detecting the magnetic media. The signals are transmitted to controller 86 to indicate whether or not the drape is properly positioned and/or present on the thermal treatment system. In response to receiving signals from detector 69 indicating the proper positioning and/or presence of the drape on the thermal treatment system, controller 86 enables thermal treatment system operation as described above. When magnetic media 67 serve as placement indicia, placement of the magnetic media on the thermal treatment system top surface at a location detectable by magnetic detector 69 typically provides and enables the magnetic detector to sense proper drape positioning on the thermal treatment system. If magnetic detector 69 does not detect magnetic media 67, the drape is either absent or improperly positioned on the thermal treatment system and controller 86 does not enable or, in other words, disables power to temperature controller 38, while power switch 37 remains illuminated. Thermal treatment system 3h typically functions to continuously monitor the drape and disable power to the temperature controller when the drape is no longer detected (e.g., the drape shifts position or is removed during system operation). However, conventional interlock circuitry may be provided as described above to maintain power to the temperature controller after initial detection of a drape until the thermal treatment system is powered down. The drape may include any quantity of magnetic media disposed within or on the drape, while the thermal treatment system may include any quantity of associated detectors disposed within the thermal treatment system whereby the detectors may be disposed within the thermal treatment system in any manner capable of detecting the magnetic media drape. The outputs of any quantity of magnetic detectors may be combined in any manner (e.g., AND, OR, etc.) to determine the proper positioning and/or presence of the drape on the thermal treatment system and enable system Ask operation (e.g., any percentage of the detectors may be required to detect the drape to enable system operation).

The magnetic drape detection technique described above may be utilized with cooling and/or warming basins of any single or multiple basin thermal treatment systems in substantially the same manner described above. The magnetic detector may be disposed at any appropriate locations to accommodate warming basin heating pads and cooling basin dislodgement mechanisms. In addition, the warming basin heating pad configurations and the infrared and magnetic drape detection techniques described above may be utilized individually or in any combination within a thermal treatment system basin.

It will be appreciated that the embodiments described above and illustrated in the drawings represent only a few of the many ways of implementing a thermal treatment system and method for maintaining integrity and ensuring sterility of surgical drapes used with surgical equipment.

The heating pads may be implemented by any conventional or other types of heating pads capable of being disposed on the basin in various configurations. The heating pad may be of any shape or size, and may be disposed on a basin of any shape or size in any configuration that does not cover substantially the entire basin. The thermostat and temperature sensor may be implemented by any conventional or other thermostats and sensors, and may be disposed at any location on the basin. The connector may be implemented by any conventional or other connector, and may be disposed on or adjacent the heating pad at any location. The heating pad may be attached to the basin via adhesives or any other fastening techniques. The warming circuit may be implemented by any conventional components or any other circuitry capable of controlling basin temperature. The heating pad configurations may be utilized with warming basins of single or multiple basin thermal treatment systems. Any quantities or types of objects may be placed within the warming basin to be heated by the basin and warmed liquid. The warming and cooling basins may contain and thermally treat any type of liquid or medium. The heating pad strips, segment portions, segments and projections may be of any quantity, size or shape, and may be disposed on the basin in any fashion. Further, the heating pad heating element may be of any size or shape, and may be disposed within the heating pad in any fashion to cover any portion of the basin.

The thermal treatment systems of the present invention are capable of including sound or visual indicators notifying when a drape is in an improper position and/or absent from the thermal treatment system. Such indicators may include an alarm, buzzer, colored light, speech synthesizer or any other indicator used for specifying a condition or state of an object.

The reflective material segment may be of any shape or size, may be disposed on the drape at any location in any quantity (e.g., at least one), and may be constructed of any material capable of reflecting infrared or other light or other signals toward the detector. The infrared light source and detectors may be disposed anywhere about or within the thermal treatment system in any quantity (e.g., at least one) and configured to emit and receive infrared or any other bands, frequencies or colors of light or other signals. The infrared light sources and detectors may be implemented by any conventional sources and detectors or any other devices capable of emitting and detecting infrared or other bands of light or other signals. The control circuitry may be implemented by conventional components (e.g., transformer, switches, opticoupler, etc.) or any other circuitry capable of enabling operation in response to drape detection.

The drape may include any magnetic media detectable by a magnetic detector whereby the magnetic media may be of any shape or size. Further, there may be any quantity of magnetic media (e.g., at least one) disposed on the drape at any location and any quantity of detectors (e.g., at least one) disposed about the thermal treatment system whereby the detectors are typically implemented by conventional magnetic detectors or any other devices capable of detecting the magnetic media. The respective outputs of the infrared and magnetic detectors may be combined in various manners (e.g., AND, OR, etc.) to detect the proper positioning and/or presence of the drape on the thermal treatment system. The window may be of any shape or size, may be disposed in the basin or thermal treatments system at any location, and may be constructed of any suitable materials (e.g., including no materials or, in other words, implemented by an opening) enabling detection of the drape. The controller of the present invention may be implemented by any conventional controller or microprocessor or other circuitry or combinational logic to enable power to the temperature controller in response to detection of a drape. The interlock circuitry may be implemented by any circuitry, microprocessor or controller capable of maintaining system operation upon initial drape detection until the system is powered down.

The principles of the present invention are not limited to thermal treatment systems including a single basin, but are equally applicable to thermal treatment systems having a plurality of basins with each basin either warming or cooling a sterile liquid. Specifically, a thermal treatment system may include a plurality of basins disposed on a top surface for either cooling or warming a sterile liquid (e.g., FIG. 5). The heating pads of the present invention may only be disposed on those basins warming the liquid in substantially the same manner described above. The heating pads heat the respective basin floors to enable the basins to absorb thermal energy and prevent the drape from absorbing excess thermal energy that may burn, melt or puncture the drape as described above. Further, the infrared and magnetic drape detection techniques described above may be utilized in multiple basin thermal treatment systems whereby drapes for these systems include reflective material segments or magnetic media corresponding to each basin, while corresponding detectors are disposed within each basin to detect the drape as described above. The respective detector outputs may be combined in various manners as described above to indicate drape detection. Alternatively, detectors may be embedded within a multiple basin thermal treatment system top surface to detect the drape as described above. The heating pad configurations and drape detection techniques described above may be utilized individually or in any combination within single or multiple basin thermal treatment systems.

From the foregoing description it will be appreciated that the invention makes available a novel thermal treatment system and method for maintaining integrity and ensuring sterility of surgical drapes used with surgical equipment wherein a heating pad is disposed on a thermal treatment system basin in various configurations to cover a portion of the basin floor and enable the basin to absorb thermal energy, thereby preventing the drape from absorbing excess thermal energy that may burn, melt or puncture the drape. Further, the drape may include reflective material or magnetic media that are detectable by a thermal treatment system to indicate the proper positioning and/or presence of the drape on the thermal treatment system to ensure sterility of a sterile liquid thermally treated by the thermal treatment system.

Having described preferred embodiments of a new and improved thermal treatment system and method for maintaining integrity and ensuring sterility of surgical drapes used with surgical equipment, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A thermal treatment system for thermally treating and ensuring sterility of a sterile medium comprising:

a basin recessed within a top surface of a system housing;

a surgical drape covering and substantially conforming to said basin to serve as a drape container for containing the sterile medium and at least one medical utensil placed within said basin, wherein said drape provides a sterile field above said basin for maintaining sterility of the sterile medium and said at least one medical utensil; and a heater disposed proximate a floor of said basin to heat the sterile medium and said at least one medical utensil contained within said drape container, wherein said heater is attached and applies thermal energy only to selected portions of said basin floor and said basin floor includes at least one basin floor section lacking coincidence with and direct application of thermal energy from said heater, and wherein said at least one medical utensil contacts said drape container at a location coincident at least one of said basin floor sections to enable said basin to absorb and disperse thermal energy in sufficient quantities to prevent damage to said drape and maintain the sterile field to ensure sterility of the sterile medium when said at least one medical utensil is placed within said basin.

2. The system of claim 1 wherein said heater includes a plurality of individual heating pad segments each attached to different selected portions of said basin floor.

3. The system of claim 1 wherein said at least one medical utensil is placed within said basin entirely coincident said at least one basin floor section lacking direct application of thermal energy from said heater to enable said selected portions to disperse thermal energy from said heater to said basin in sufficient quantities to protect said drape.

4. The system of claim 1 wherein said heater includes a plurality of openings defined therein, and said basin includes a plurality of said basin floor sections each disposed coincident a corresponding heater opening.

5. A thermal treatment system for thermally treating and ensuring sterility of a sterile medium comprising:

a basin recessed within a top surface of a system housing;

a surgical drape covering and substantially conforming to said basin to serve as a drape container for containing the sterile medium and at least one medical utensil placed within said basin, wherein said drape provides a sterile field above said basin for maintaining sterility of the sterile medium and said at least one medical utensil; and a heater disposed proximate a floor of said basin to heat the sterile medium and said at least one medical utensil contained within said drape container, wherein said heater includes a heating pad attached to and covering substantially the entire basin floor and a heating element disposed within said heating pad and applying thermal energy only to selected portions of said basin floor;

wherein said basin floor includes at least one basin floor section lacking coincidence with and direct application of thermal energy from said heating element, and wherein said at least one medical utensil contacts said drape container at a location coincident at least one of said basin floor sections to enable said basin to absorb and disperse thermal energy in sufficient quantities to prevent damage to said drape and maintain the sterile field to ensure sterility of the sterile medium when said at least one medical utensil is placed within said basin.

6. The system of claim 1 further including:

a plurality of basins disposed within said top surface, wherein said surgical drape covers and substantially conforms to each said basin to serve as drape containers to contain the sterile medium and to provide the sterile field above each basin for maintaining sterility of the sterile medium, and wherein said at least one medical utensil is placed within one or more of said basins; and at least one heater with each basin containing said at least one medical utensil having a corresponding heater disposed proximate a floor of that basin to heat the sterile medium and said at least one medical utensil placed within that basin, wherein each said corresponding heater is attached and applies thermal energy only to selected portions of a floor of said corresponding basin, and said corresponding basin includes at least one basin floor section lacking coincidence with and direct application of thermal energy from an associated heater, and wherein said at least one medical utensil contacts a drape container of said corresponding basin at a location coincident at least one of said basin floor sections of said corresponding basin to enable said each corresponding basin to absorb and disperse thermal energy in sufficient quantities to prevent damage to said drape and maintain the sterile field to ensure sterility of the sterile medium when said at least one medical utensil is placed within that basin.

7. In a thermal treatment system for thermally treating a sterile medium including a basin recessed in a top surface of a system housing, a heater disposed proximate a floor of the basin and a surgical drape covering and substantially conforming to said basin to serve as a drape container for containing the sterile medium and at least one medical utensil placed within the basin, wherein the drape provides a sterile field above the basin for maintaining sterility of the sterile medium and said at least one medical utensil, a method of thermally treating and ensuring sterility of the sterile medium comprising the steps of:

(a) applying thermal energy only to selected portions and less than the entirety of said basin floor via said heater; and (b) in response to placement of said at least one medical utensil within said basin, ensuring sterility of the sterile medium and protecting said drape from damage due to absorption of thermal energy in excess of a drape tolerance by dispersing said thermal energy from said selected portions of said basin floor to said basin in quantities within said drape tolerance.

8. The method of claim 7 wherein step (a) further includes:

(a.1) placing said at least one medical utensil within said basin partially coincident said selected portions of the basin floor to enable said selected portions to disperse thermal energy from said heater to said basin in quantities within said drape tolerance.

9. The method of claim 7 wherein step (a) further includes:

(a.1) placing said at least one medical utensil within said basin entirely coincident portions of the basin floor lacking direct application of thermal energy from said heater to enable said selected portions to disperse thermal energy from said heater to said basin in quantities within said drape tolerance.

10. The method of claim 7 wherein step (a) further includes:

(a.1) covering the selected portions and less than the entirety of said basin floor with said heater to enable said selected portions to disperse thermal energy from said heater to said basin in quantities within said drape tolerance.

11. The method of claim 7 wherein said heater includes a heating pad configured to cover substantially the entire basin floor and a heating element disposed within the heating pad, and step (a) further includes:
  (a.1) applying thermal energy only to the selected portions and less than the entirety of said basin floor via said heating element.

12. The method of claim 7 wherein said thermal treatment system further includes a plurality of basins disposed within said top surface with said at least one medical utensil placed in one or more of said basins and at least one heater with each basin containing said at least one medical utensil having a corresponding heater disposed proximate a floor of that basin to heat the sterile medium and said at least one medical utensil placed within that basin, wherein said surgical drape covers and substantially conforms to each said basin to serve as drape containers to contain the sterile medium and to provide the sterile field above each basin for maintaining sterility of the sterile medium, and step (a) further includes:
  (a.1) applying thermal energy only to selected portions and less than the entirety of a floor of each basin containing said at least one medical utensil via said heater corresponding to that basin; and
  step (b) further includes:
  (b.1) in response to placement of said at least one medical utensil within one or more of said basins, ensuring sterility of the sterile medium and protecting said drape from damage due to absorption of thermal energy in excess of said drape tolerance by dispersing said thermal energy from said selected portions of said floors of said basins containing said at least one medical utensil to those basins in quantities within said drape tolerance.

13. A thermal treatment system for thermally treating and ensuring sterility of a sterile medium comprising:
  a basin recessed within a top surface of a system housing for receiving a surgical drape substantially conforming to said basin to serve as a drape container for containing the sterile medium, wherein said drape provides a sterile field above said basin for maintaining sterility of the sterile medium; and
  a heater disposed proximate a floor of said basin to heat the sterile medium contained within said drape container, wherein said heater is attached and applies thermal energy only to selected portions of said basin floor and said basin floor includes at least one basin floor section lacking coincidence with and direct application of thermal energy from said heater to facilitate dispersion of said thermal energy from said selected portions to said basin in quantities within a tolerance of said drape in response to placement of at least one medical utensil within said drape container, thereby preventing damage to said drape and maintaining the sterile field to ensure sterility of the sterile medium.

14. The system of claim 13 wherein said heater includes a plurality of individual heating pad segments each attached to different selected portions of said basin floor.

15. A thermal treatment system for thermally treating and ensuring sterility of a sterile medium comprising:
  a basin recessed within a top surface of a system housing for receiving a surgical drape substantially conforming to said basin to serve as a drape container for containing the sterile medium, wherein said drape provides a sterile field above said basin for maintaining sterility of the sterile medium; and
  a heater disposed proximate a floor of said basin to heat the sterile medium contained within said drape container, wherein said heater includes a heating pad attached to and covering substantially the entire basin floor and a heating element disposed within said heating pad applying thermal energy only to selected portions of said basin floor;
  wherein said basin floor includes at least one basin floor section lacking coincidence with and direct application of thermal energy from said heating element to facilitate dispersion of said thermal energy from said selected portions to said basin in quantities within a tolerance of said drape in response to placement of at least one medical utensil within said drape container, thereby preventing damage to said drape and maintaining the sterile field to ensure sterility of the sterile medium.

16. The system of claim 13 further including:
  a plurality of basins disposed within said top surface, wherein said surgical drape covers and substantially conforms to each said basin to serve as drape containers to contain the sterile medium and to provide the sterile field above each basin for maintaining sterility of the sterile medium, wherein at least one basin heats the sterile medium; and
  at least one heater with each basin heating the sterile medium having a corresponding heater disposed proximate a floor of that basin to heat the sterile medium, wherein each said corresponding heater is attached and applies thermal energy to only selected portions of a floor of a corresponding heated basin and said floor of said corresponding heated basin includes at least one basin floor section lacking coincidence with and direct application of thermal energy from said corresponding heater to facilitate dispersion of said thermal energy from said selected portions to said corresponding basin in quantities within a tolerance of said drape in response to placement of at least one medical utensil within said drape container of said corresponding basin, thereby preventing damage to said drape and maintaining the sterile field to ensure sterility of the sterile medium.

17. The method of claim 7 wherein said heater includes a plurality of individual heating pad segments each disposed coincident different selected portions of said basin floor, and step (a) further includes:
  (a.1) applying thermal energy only to said selected portions of said basin floor via said heating pad segments.

18. The method of claim 7 wherein said heater includes a plurality of openings defined therein, and step (a) further includes:
  (a.1) applying thermal energy to only said selected portions and less than the entirety of said basin floor via said openings within said heater.

19. The system of claim 13 wherein said heater includes a plurality of individual heating pad segments each attached to different selected portions of said basin floor.

20. The system of claim 13 wherein said heater includes a plurality of openings defined therein, and said basin includes a plurality of said basin floor sections each disposed coincident a corresponding heater opening.

* * * * *